United States Patent
Kadota et al.

(10) Patent No.: US 10,316,026 B2
(45) Date of Patent: Jun. 11, 2019

(54) METHOD FOR REMOVING DIMETHOXYBENZYL GROUP

(71) Applicant: DAIICHI SANKYO COMPANY, LIMITED, Tokyo (JP)

(72) Inventors: Kohei Kadota, Tokyo (JP); Tsuyoshi Ueda, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/760,411

(22) PCT Filed: Nov. 4, 2016

(86) PCT No.: PCT/JP2016/082752
§ 371 (c)(1),
(2) Date: Mar. 15, 2018

(87) PCT Pub. No.: WO2017/078123
PCT Pub. Date: May 11, 2017

(65) Prior Publication Data
US 2018/0251448 A1    Sep. 6, 2018

Related U.S. Application Data

(63) Continuation of application No. PCT/JP2016/082752, filed on Nov. 4, 2016.

(30) Foreign Application Priority Data

Nov. 6, 2015 (JP) .................... 2015-218355

(51) Int. Cl.
C07D 213/76    (2006.01)
C07D 239/69    (2006.01)
C07D 277/52    (2006.01)
C07D 403/12    (2006.01)

(52) U.S. Cl.
CPC ......... C07D 403/12 (2013.01); C07D 213/76 (2013.01); C07D 239/69 (2013.01); C07D 277/52 (2013.01)

(58) Field of Classification Search
CPC ............. C07D 403/12; C07D 277/52; C07D 213/76; C07D 239/69
See application file for complete search history.

(56) References Cited

U.S. PATENT DOCUMENTS

| 2012/0010182 A1 | 1/2012 | Brown et al. |
| 2014/0296245 A1 | 10/2014 | Sun et al. |
| 2015/0018551 A1 | 1/2015 | Shinozuka et al. |

FOREIGN PATENT DOCUMENTS

| EP | 2 813 491 A1 | 2/2013 | |
| EP | 2813491 A1 * | 12/2014 | ........... C07D 403/12 |
| JP | 2012-515156 A | 7/2012 | |
| JP | 2013-531031 A | 8/2013 | |
| JP | 2014-532640 A | 12/2014 | |
| WO | WO-2010/079443 A1 | 7/2010 | |
| WO | WO-2010079443 A1 * | 7/2010 | ........... C07D 263/50 |
| WO | WO-2012/004743 A1 | 1/2012 | |
| WO | WO-2013/064983 A1 | 5/2013 | |
| WO | WO-2013/118854 A1 | 8/2013 | |
| WO | WO-2014/066490 A1 | 5/2014 | |
| WO | WO-2014066490 A1 * | 5/2014 | ........... C07D 263/58 |

OTHER PUBLICATIONS

Wuts, P. G. M. and Greene, T. W. in Greene's Protective Groups in Organic Synthesis, 4th Ed. New Jersey: John Wiley & Sons, Inc. 2007. (Year: 2007).*
Greens Protective Groups in Organic Synthesis, Wuts, Peter G, Wiley, Fifth Edition. 2014.
Protective Groups in Organic Synthesis, Greene et al, John Wiley & Sons, Inc., Third Edition. 1999.
Wuts et al., "Protection for the Amino Group," Greene's Protective Groups in Organic Synthesis, Fourth Edition, 2007, pp. 696-926.
European Patent Office, "Communication with Supplementary European Search Report," issued in connection with European Patent Application No. 16862183.7, dated May 7, 2019.

* cited by examiner

*Primary Examiner* — Amanda L Aguirre
(74) *Attorney, Agent, or Firm* — Foley & Lardner LLP

(57) ABSTRACT

In a method for producing a de-dimethoxybenzylated compound by removing a dimethoxybenzyl group from a compound containing a dimethoxybenzyl group bonded to a nitrogen atom in the presence of an acid, the de-dimethoxybenzylated compound is obtained by removing the dimethoxybenzyl group without forming a poorly soluble product resulting from the removed dimethoxybenzyl group. The de-dimethoxybenzylation reaction is carried out in the presence of triphenylphosphine or diethylthiourea.

29 Claims, 1 Drawing Sheet

METHOD FOR REMOVING DIMETHOXYBENZYL GROUP

CROSS-REFERENCE TO RELATED APPLICATIONS

The present application is a U.S. national stage application of International Patent Application No. PCT/JP2016/082752, filed Nov. 4, 2016, which claims the benefit of priority to Japanese Patent Application No. 2015-218355, filed Nov. 6, 2015, the entireties of which are incorporated herein by reference.

TECHNICAL FIELD

The present invention relates to a method for removing a dimethoxybenzyl group, which is generally used as a protecting group, by acid treatment without forming a poorly soluble product.

BACKGROUND ART

In the field of organic synthetic chemistry, an approach of protecting functional groups with protecting groups is often adopted in order to prevent unintended chemical reactions. Various groups are known as such protecting groups. For example, a benzyl group is generally used for the protection of —OH or >NH in a carboxy group, a hydroxyl group, an amino group, an amide group, a sulfonamide group, and the like. In most cases, protecting groups are to be removed at any stage and thus have the property of being easily cleavable according to need. The benzyl group usually has the property of being easily cleaved by hydrogenolysis reaction, oxidation reaction, or treatment with a Lewis acid or the like, and is frequently used. Also, a methoxy-substituted benzyl group in which 1 to 3 methoxy groups are introduced in the phenyl group of the benzyl group particularly has the property of being also eliminable by acid treatment and is advantageous in that this group can be removed without adopting reductive conditions (Non-Patent Literature 1).

A compound having a benzenesulfonamide structure is known as an analgesically active compound. In the production of this compound, an intermediate containing a 2,4-dimethoxybenzyl group bonded to the nitrogen atom of a sulfonamide group is adopted and converted to the objective compound through cleavage of this 2,4-dimethoxybenzyl group by acid treatment (Patent Literatures 1 to 4).

CITATION LIST

Patent Literature

Patent Literature 1: International Publication No. WO2010/079443
Patent Literature 2: International Publication No. WO2012/004743
Patent Literature 3: International Publication No. WO2013/064983
Patent Literature 4: International Publication No. WO2013/118854

Non-Patent Literature

Non-Patent Literature 1: Theodora W. Greene, Peter G. M. Wuts, "Protective Groups in Organic Synthesis, Third Edition"; 1999, John Wiley & sons, Inc.

SUMMARY OF INVENTION

Technical Problem

For the production of an analgesically active compound having a benzenesulfonamide structure, a complex operation is performed for the isolation of a compound from which a 2,4-dimethoxybenzyl group has been removed, in the step of removing this group. Thus, it is understood that this step has a difficulty in isolating or obtaining the objective compound (Patent Literatures 1 to 3).

The present inventors have also adopted a production intermediate containing a 2,4-dimethoxybenzyl group bonded to the nitrogen atom of a sulfonamide group for the production of their objective benzenesulfonamide compound, and performed the removal thereof by acid treatment. It has been revealed that although the removal itself of this 2,4-dimethoxybenzyl group proceeds without problems by the acid treatment, the objective compound is contaminated by a poorly soluble product considered to be formed in such a way that the removed 2,4-dimethoxybenzyl group reacts complicatedly. This product is a complex mixture and is poorly soluble in both organic solvents and aqueous solvents. Hence, it has been found that the removal thereof is very cumbersome, and that the poorly soluble product requires a great deal of labor for the isolation and purification of the objective compound and also influences yields and product purity.

Specifically, for the removal of a dimethoxybenzyl group under acidic conditions from a benzenesulfonamide compound containing a dimethoxybenzyl group bonded to the nitrogen atom of a sulfonamide group, there is a need for a method for removing the dimethoxybenzyl group without forming a poorly soluble product.

Solution to Problem

The present inventors have earnestly conducted studies and consequently confirmed that for the removal of a dimethoxybenzyl group by acid treatment of a benzenesulfonamide compound containing the dimethoxybenzyl group bonded to the nitrogen atom of a sulfonamide group, the reaction can be carried out in the presence of coexisting triphenylphosphine to thereby obtain the objective de-dimethoxybenzylated compound without forming a poorly soluble product.

The present inventors have further confirmed that the reaction can also be performed in the presence of coexisting diethylthiourea instead of triphenylphosphine to thereby obtain the de-dimethoxybenzylated compound without forming a poorly soluble product.

The present invention has been completed on the basis of these excellent effects thus confirmed.

Specifically, the present invention relates to:

[1] A method for producing a de-dimethoxybenzylated compound, comprising treating a compound containing a dimethoxybenzyl group bonded to a nitrogen atom with an acid to remove the dimethoxybenzyl group, wherein the method is carried out in the presence of triphenylphosphine or diethylthiourea.

The present invention further relates to the following:

[2] The method according to [1], wherein the removal of the dimethoxybenzyl group is carried out in the presence of triphenylphosphine.

[3] The method according to [1] or [2], wherein the dimethoxybenzyl group is a 2,3-dimethoxybenzyl group, a 2,4-dimethoxybenzyl group, a 2,5-dimethoxybenzyl group, a 2,6-dimethoxybenzyl group, a 3,4-dimethoxybenzyl group, or a 3,5-dimethoxybenzyl group.

[4] The method according to [1] or [2], wherein the dimethoxybenzyl group is a 2,4-dimethoxybenzyl group.

[5] The method according to any one of [1] to [4], wherein the acid is a strong acid.

[6] The method according to any one of [1] to [4], wherein the acid is hydrochloric acid, methanesulfonic acid, trifluoromethanesulfonic acid, benzenesulfonic acid, toluenesulfonic acid, or trifluoroacetic acid.

[7] The method according to any one of [1] to [4], wherein the acid is hydrochloric acid.

[8] The method according to any one of [1] to [7], wherein the nitrogen atom to which the dimethoxybenzyl group is bonded is a nitrogen atom constituting a sulfonamide group.

[9] The method according to [8], wherein the sulfonamide group with the dimethoxybenzyl group bonded to the nitrogen atom is a sulfonamide group of a benzenesulfonamide compound.

[10] The method according to [9], wherein the benzenesulfonamide compound having the sulfonamide group with the dimethoxybenzyl group bonded to the nitrogen atom is
5-chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide,
5-chloro-N-(2,4-dimethoxybenzyl)-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide,
5-chloro-N-(2,4-dimethoxybenzyl)-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide,
5-chloro-N-(2,4-dimethoxybenzyl)-2-fluoro-4-{[(1S,2R,5S)-5-hydroxy-2-(1-methyl -1H-pyrazol-5-yl)cyclohexyl]oxy}-N-(pyrimidin-4-yl)benzenesulfonamide,
4-{[(3R,4S)-4-(4-chlorophenyl)piperidin-3-yl]methoxy}-2,5-difluoro-N-(2,4-dimethoxybenzyl)-N-(5-fluoropyrimidin-2-yl)benzenesulfonamide, or
3-cyano-N-(2,4-dimethoxybenzyl)-4-[2-(2-methylpyrazol-3-yl)phenoxy]-N-thiazol-2-yl-benzenesulfonamide.

The respective resulting products are as follows:
5-chloro-2-fluoro-4-{[(1S,2R)-2-(1-methyl-1H-pyrazol-5-yl)cyclohexyl]oxy}-N-(pyrimidin-4-yl)benzenesulfonamide,
5-chloro-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide,
5-chloro-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide,
5-chloro-2-fluoro-4-{[(1S,2R,5S)-5-hydroxy-2-(1-methyl-1H-pyrazol-5-yl)cyclohexyl]oxy}-N-(pyrimidin-4-yl)benzenesulfonamide,
4-{[(3R,4S)-4-(4-chlorophenyl)piperidin-3-yl]methoxy}-2,5-difluoro-N-(5-fluoropyrimidin-2-yl)benzenesulfonamide, and
3-cyano-4-[2-(2-methylpyrazol-3-yl)phenoxy]-N-thiazol-2-yl-benzenesulfonamide.

[11] The method according to [9], wherein the benzenesulfonamide compound having the sulfonamide group with the dimethoxybenzyl group bonded to the nitrogen atom is
5-chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide,
5-chloro-N-(2,4-dimethoxybenzyl)-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide,
5-chloro-N-(2,4-dimethoxybenzyl)-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide, or
5-chloro-N-(2,4-dimethoxybenzyl)-2-fluoro-4-{[(1S,2R,5S)-5-hydroxy-2-(1-methyl-1H-pyrazol-5-yl)cyclohexyl]oxy}-N-(pyrimidin-4-yl)benzenesulfonamide.

[12] The method according to [1], wherein the compound containing a dimethoxybenzyl group bonded to a nitrogen atom is
5-chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide,
5-chloro-N-(2,4-dimethoxybenzyl)-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide,
5-chloro-N-(2,4-dimethoxybenzyl)-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide, or
5-chloro-N-(2,4-dimethoxybenzyl)-2-fluoro-4-{[(1S,2R,5S)-5-hydroxy-2-(1-methyl-1H-pyrazol-5-yl)cyclohexyl]oxy}-N-(pyrimidin-4-yl)benzenesulfonamide.

[13] A method for producing a compound represented by the formula given below, comprising treating a compound represented by the following formula containing a dimethoxybenzyl group bonded to the nitrogen atom of a sulfonamide group:

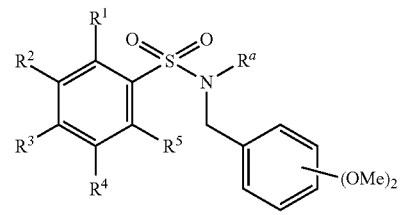

[Formula 1]

wherein $R^a$ represents an aromatic group optionally having a substituent(s), $R^1$, $R^2$, $R^4$ and $R^5$ each independently represent a hydrogen atom, a halogen atom, or an alkyl group having a carbon number of 1 to 6, and $R^3$ represents a hydrogen atom, a halogen atom, an alkyl group having a carbon number of 1 to 6, or a group represented by the following formula:

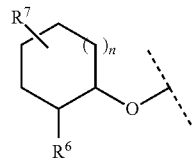

[Formula 2]

wherein n represents an integer of 0, 1, or 2, $R^6$ represents an aromatic group optionally having a substituent(s), and $R^7$ represents a hydrogen atom, a hydroxyl group, or one or two halogen atoms, wherein the group is bonded at its oxygen atom to the benzene ring, in the presence of an acid and in the presence of coexisting triphenylphosphine or diethylthiourea to produce the compound represented by the formula:

[Formula 3]

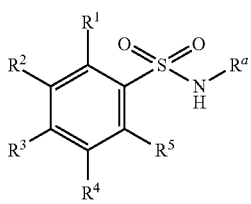

wherein $R^a$, $R^1$, $R^2$, $R^3$, $R^4$ and $R^5$ are as defined above.

[14] The method according to [13], wherein the treatment is a treatment in the presence of coexisting triphenylphosphine.

[15] The method according to [13] or [14], wherein the dimethoxybenzyl group is a 2,3-dimethoxybenzyl group, a 2,4-dimethoxybenzyl group, a 2,5-dimethoxybenzyl group, a 2,6-dimethoxybenzyl group, a 3,4-dimethoxybenzyl group, or a 3,5-dimethoxybenzyl group.

[16] The method according to [13] or [14], wherein the dimethoxybenzyl group is a 2,4-dimethoxybenzyl group.

[17] The method according to any one of [13] to [16], wherein the acid is a strong acid.

[18] The method according to any one of [13] to [16], wherein the acid is hydrochloric acid, methanesulfonic acid, trifluoromethanesulfonic acid, benzenesulfonic acid, toluenesulfonic acid, or trifluoroacetic acid.

[19] The method according to any one of [13] to [16], wherein the acid is hydrochloric acid.

[20] The method according to any one of [13] to [19], wherein $R^a$ is an aromatic heterocyclic group optionally having a substituent(s).

[21] The method according to [20], wherein $R^a$ is a thiazolyl group, thiadiazolyl group, or pyrimidyl group optionally having a substituent(s).

[22] The method according to [21], wherein $R^a$ is a pyrimidyl group optionally having a substituent(s).

[23] The method according to [22], wherein $R^a$ is a 2-pyrimidyl group or 4-pyrimidyl group optionally having a substituent(s).

[24] The method according to [22], wherein $R^a$ is a 4-pyrimidyl group optionally having a substituent(s).

[25] The method according to any one of [13] to [24], wherein $R^3$ is a group represented by the following formula:

[Formula 4]

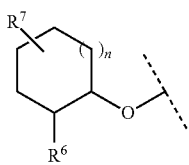

wherein the binding position of the group to the benzene ring, $R^6$, $R^7$ and n are as defined above.

[26] The method according to [25], wherein the group represented by the formula:

[Formula 5]

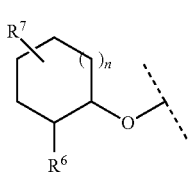

is a group having a conformation represented by the following formula:

[Formula 6]

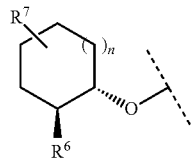

wherein the binding position of this group to the benzene ring, $R^6$, $R^7$ and n are as defined above.

[27] The method according to [25] or [26], wherein n is 1.

[28] The method according to any one of [25] to [27], wherein $R^6$ is a phenyl group, pyrrolyl group, pyrazolyl group, imidazolyl group, thiazolyl group, thiadiazolyl group, pyridyl group, pyridazinyl group, pyrimidyl group, or pyrazyl group optionally having a substituent(s).

[29] The method according to any one of [25] to [27], wherein $R^6$ is a phenyl group, pyrazolyl group, imidazolyl group, pyridyl group, or pyridazinyl group optionally having a substituent(s).

[30] The method according to any one of [13] to [27], wherein $R^6$ is a pyrazolyl group optionally having a substituent(s).

[31] The method according to [30], wherein the pyrazolyl group is a 1H-pyrazol-4-yl group or a 1H-pyrazol-5-yl group.

[32] The method according to [31], wherein the pyrazolyl group is a 1H-pyrazol-5-yl group.

[33] The method according to any one of [30] to [32], wherein the substituent(s) on the aromatic group optionally having a substituent(s), represented by $R^6$ is 1 to 3 groups selected from the group consisting of an amino group, a methyl group, an ethyl group, a fluorine atom and a chlorine atom.

[34] The method according to any one of [25] to [30], wherein $R^6$ is a 1-methyl-1H-pyrazol-5-yl group.

[35] The method according to any one of [25] to [34], wherein $R^7$ is a hydrogen atom.

[36] The method according to any one of [25] to [34], wherein $R^7$ is a hydroxyl group.

[37] A method for producing a compound represented by the formula given below, comprising treating a compound represented by the following formula in which a nitrogen atom is substituted by a dimethoxybenzyl group:

[Formula 7]

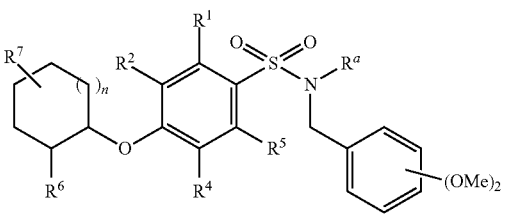

wherein $R^a$ represents an aromatic group optionally having a substituent(s), $R^1$, $R^2$, $R^4$ and $R^5$ each independently represent a hydrogen atom, a halogen atom, or an alkyl group having a carbon number of 1 to 6, $R^6$ represents an aromatic group optionally having a substituent(s), $R^7$ represents a hydrogen atom, a hydroxyl group, or one or two halogen atoms, and n represents an integer of 0, 1, or 2, in the presence of an acid and in the presence of triphenylphosphine or diethylthiourea to produce the compound represented by the formula:

[Formula 8]

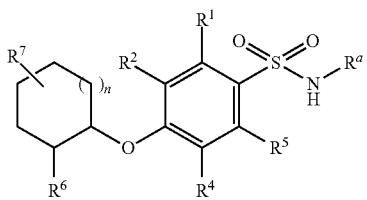

wherein $R^a$, $R^1$, $R^2$, $R^4$, $R^5$, $R^6$, $R^7$ and n are as defined above.

[38] The method according to [37], wherein the compound represented by the following formula:

[Formula 9]

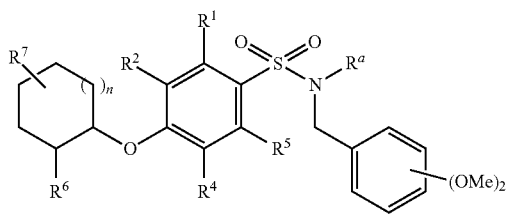

has a structure represented by the following formula:

[Formula 10]

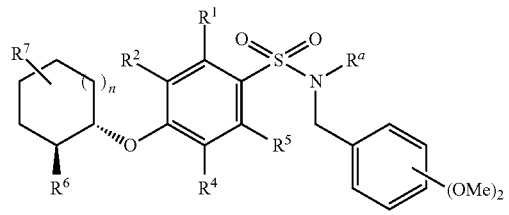

and the compound represented by the following formula:

[Formula 11]

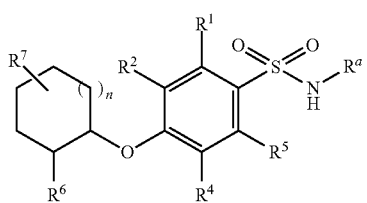

has a structure represented by the following formula:

[Formula 12]

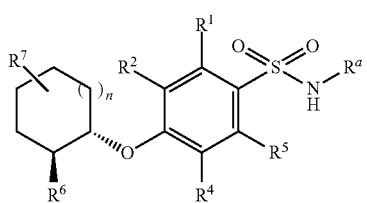

wherein $R^a$, $R^1$, $R^2$, $R^4$, $R^5$, $R^6$, $R^7$ and n are as defined above.

[39] The method according to [37] or [38], wherein the treatment is a treatment in the presence of coexisting triphenylphosphine.

[40] The method according to any one of [37] to [39], wherein the dimethoxybenzyl group is a 2,3-dimethoxybenzyl group, a 2,4-dimethoxybenzyl group, a 2,5-dimethoxybenzyl group, a 2,6-dimethoxybenzyl group, a 3,4-dimethoxybenzyl group, or a 3,5-dimethoxybenzyl group.

[41] The method according to any one of [37] to [39], wherein the dimethoxybenzyl group is a 2,4-dimethoxybenzyl group.

[42] The method according to any one of [37] to [41], wherein the acid is a strong acid.

[43] The method according to any one of [37] to [41], wherein the acid is hydrochloric acid, methanesulfonic acid, trifluoromethanesulfonic acid, benzenesulfonic acid, toluenesulfonic acid, or trifluoroacetic acid.

[44] The method according to any one of [37] to [41], wherein the acid is hydrochloric acid.

[45] The method according to any one of [37] to [44], wherein $R^a$ is an aromatic heterocyclic group optionally having a substituent(s).

[46] The method according to [45], wherein $R^a$ is a thiazolyl group, thiadiazolyl group, or pyrimidyl group optionally having a substituent(s).

[47] The method according to [46], wherein $R^a$ is a 2-pyrimidyl group or 4-pyrimidyl group optionally having a substituent(s).

[48] The method according to [46], wherein $R^a$ is a 4-pyrimidyl group optionally having a substituent(s).

[49] The method according to any one of [37] to [48], wherein n is 1.

[50] The method according to any one of [37] to [49], wherein $R^6$ is a phenyl group, pyrazolyl group, imidazolyl group, pyridyl group, or pyridazinyl group optionally having a substituent(s).

[51] The method according to any one of [37] to [49], wherein $R^6$ is a pyrazolyl group optionally having a substituent(s).

[52] The method according to [51], wherein $R^6$ is a 1H-pyrazol-5-yl group optionally having a substituent(s).

[53] The method according to [52], wherein the substituent(s) on the aromatic group optionally having a substituent(s), represented by $R^6$ is 1 to 3 groups selected from the group consisting of an amino group, a methyl group, an ethyl group, a fluorine atom and a chlorine atom.

[54] The method according to any one of [37] to [50], wherein $R^6$ is a 1-methyl-1H-pyrazol-5-yl group.

[55] The method according to any one of [37] to [54], wherein $R^7$ is a hydrogen atom.

[56] The method according to any one of [37] to [54], wherein $R^7$ is a hydroxyl group.

[57] The method according to [37], wherein the compound represented by the formula:

[Formula 13]

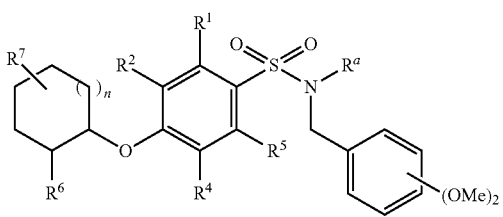

is
5-chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide,
5-chloro-N-(2,4-dimethoxybenzyl)-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide,
5-chloro-N-(2,4-dimethoxybenzyl)-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide, or
5-chloro-N-(2,4-dimethoxybenzyl)-2-fluoro-4-{[(1S,2R,5S)-5-hydroxy-2-(1-methyl-1H-pyrazol-5-yl)cyclohexyl]oxy}-N-(pyrimidin-4-yl)benzenesulfonamide.
The respective resulting products are as follows:
5-chloro-2-fluoro-4-{[(1S,2R)-2-(1-methyl-1H-pyrazol-5-yl)cyclohexyl]oxy}-N-(pyrimidin-4-yl)benzenesulfonamide,
5-chloro-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide,
5-chloro-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide, and
5-chloro-2-fluoro-4-{[(1S,2R,5S)-5-hydroxy-2-(1-methyl-1H-pyrazol-5-yl)cyclohexyl]oxy}-N-(pyrimidin-4-yl)benzenesulfonamide.

[58] The method according to [37], wherein the compound represented by the formula:

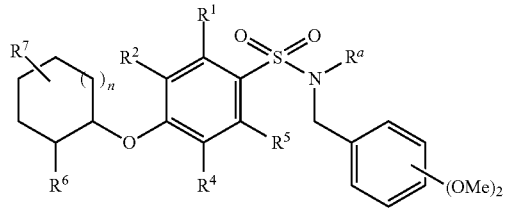

[Formula 14]

is 5-chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide.
The resulting product is 5-chloro-2-fluoro-4-{[(1S,2R)-2-(1-methyl-1H-pyrazol-5-yl)cyclohexyl]oxy}-N-(pyrimidin-4-yl)benzenesulfonamide.

[59] The method according to [37], wherein the compound represented by the formula:

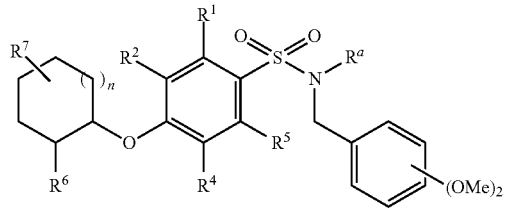

[Formula 15]

is 5-chloro-N-(2,4-dimethoxybenzyl)-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide.
The resulting product is 5-chloro-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide.

[60] The method according to [37], wherein the compound represented by the formula:

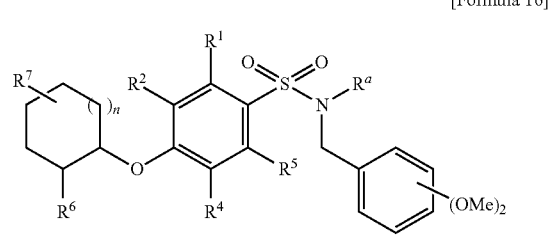

[Formula 16]

is 5-chloro-N-(2,4-dimethoxybenzyl)-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide.
The resulting product is 5-chloro-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide.

[61] The method according to [37], wherein the compound represented by the formula:

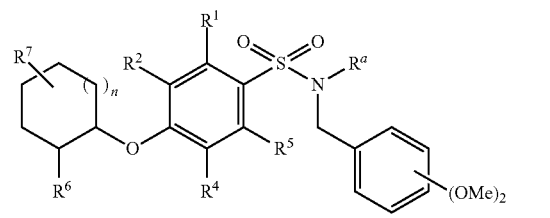

[Formula 17]

is 5-chloro-N-(2,4-dimethoxybenzyl)-2-fluoro-4-{[(1S,2R,5S)-5-hydroxy-2-(1-methyl-1H-pyrazol-5-yl)cyclohexyl]oxy}-N-(pyrimidin-4-yl)benzenesulfonamide.
The resulting product is 5-chloro-2-fluoro-4-{[(1S,2R,5S)-5-hydroxy-2-(1-methyl-1H-pyrazol-5-yl)cyclohexyl]oxy}-N-(pyrimidin-4-yl)benzenesulfonamide.

[62] The method according to [13], wherein $R^3$ is a group represented by the following formula:

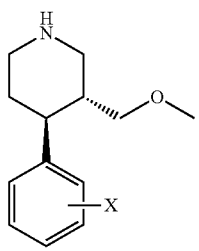

[Formula 18]

wherein X represents 1 or 2 groups selected from the group consisting of a hydrogen atom, a fluorine atom, a chlorine atom and a methyl group, the oxygen atom of the methyleneoxy is the binding site, and in the benzene ring bonded to the piperidine, the position number of the carbon atom bonded to the piperidine ring is 1.

[63] The method according to [62], wherein X is a hydrogen atom, a 4-fluorine atom, a 4-chlorine atom, a 3,4-difluorine atom, a 3-fluorine atom-4-chlorine atom, or a 4-methyl group.

[64] The method according to [62], wherein X is mono-substituted and is a 4-fluorine atom or a 4-chlorine atom.

[65] The method according to [62], wherein X is mono-substituted and is a 4-chlorine atom.

[66] The method according to any one of [62] to [65], wherein $R^a$ is a 1,3-thiazol-2-yl group, 1,2-oxazol-3-yl group, 1,2,4-thiazol-5-yl group, 1,3,4-thiazol-2-yl group, pyridin-2-yl group, pyridazin-3-yl group, pyrimidin-2-yl group, or pyrimidin-4-yl group optionally having a substituent(s).

[67] The method according to any one of [62] to [65], wherein $R^a$ is a 5-methyl-1,3-thiazol-2-yl group, a 5-chloro-1,3-thiazol-2-yl group, a 1,3,4-thiazol-2-yl group, a 5-fluoro-pyridin-2-yl group, a pyridazin-3-yl group, a pyrimidin-2-yl group, a 5-fluoro-pyrimidin-2-yl group, or a pyrimidin-4-yl group.

[68] The method according to any one of [62] to [65], wherein $R^a$ is a 5-fluoro-pyrimidin-2-yl group, and each of $R^1$ and $R^4$ is a fluorine atom, and each of $R^2$ and $R^5$ is a hydrogen atom.

[69] A method for removing a dimethoxybenzyl group bonded to a nitrogen atom, wherein the method is carried out in the presence of an acid and in the presence of coexisting triphenylphosphine or diethylthiourea.

[70] The method according to [69], wherein the method is carried out in the presence of coexisting triphenylphosphine.

[71] The method according to [69] or [70], wherein the dimethoxybenzyl group is a 2,3-dimethoxybenzyl group, a 2,4-dimethoxybenzyl group, a 2,5-dimethoxybenzyl group, a 2,6-dimethoxybenzyl group, a 3,4-dimethoxybenzyl group, or a 3,5-dimethoxybenzyl group.

[72] The method according to [69] or [70], wherein the dimethoxybenzyl group is a 2,4-dimethoxybenzyl group.

[73] The method according to any one of [69] to [72], wherein the acid is a strong acid.

[74] The method according to any one of [69] to [72], wherein the acid is hydrochloric acid, methanesulfonic acid, trifluoromethanesulfonic acid, benzenesulfonic acid, toluenesulfonic acid, or trifluoroacetic acid.

[75] The method according to any one of [69] to [72], wherein the acid is hydrochloric acid.

[76] The method according to any one of [69] to [72], wherein the nitrogen atom to which the dimethoxybenzyl group is bonded is a nitrogen atom constituting a sulfonamide group of a benzenesulfonamide compound.

[77] The method according to [76], wherein the benzenesulfonamide compound is a benzenesulfonamide compound having a substituent(s) on its benzene ring, wherein an aromatic group optionally having a substituent(s) is further bonded to the nitrogen atom of the sulfonamide group to which the dimethoxybenzyl group is bonded.

[78] The method according to [77], wherein the benzenesulfonamide compound is
5-chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide,
5-chloro-N-(2,4-dimethoxybenzyl)-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide,
5-chloro-N-(2,4-dimethoxybenzyl)-2-fluoro-4-{[(1S,2R,5S)-5-hydroxy-2-(1-methyl-1H-pyrazol-5-yl)cyclohexyl]oxy}-N-(pyrimidin-4-yl)benzenesulfonamide,
4-{[(3R,4S)-4-(4-chlorophenyl)piperidin-3-yl]methoxy}-2,5-difluoro-N-(2,4-dimethoxybenzyl)-N-(5-fluoropyrimidin-2-yl)benzenesulfonamide, or
3-cyano-N-(2,4-dimethoxybenzyl)-4-[2-(2-methylpyrazol-3-yl)phenoxy]-N-thiazol-2-yl-benzenesulfonamide.

[79] The method according to [77], wherein the benzenesulfonamide compound containing the dimethoxybenzyl group bonded to the nitrogen atom is
5-chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide,
5-chloro-N-(2,4-dimethoxybenzyl)-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide,
5-chloro-N-(2,4-dimethoxybenzyl)-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide, or
5-chloro-N-(2,4-dimethoxybenzyl)-2-fluoro-4-{[(1S,2R,5S)-5-hydroxy-2-(1-methyl-1H-pyrazol-5-yl)cyclohexyl]oxy}-N-(pyrimidin-4-yl)benzenesulfonamide.

[80] A method for suppressing the formation of a poorly soluble reaction product in a removal reaction of a dimethoxybenzyl group bonded to a nitrogen atom under acidic conditions, comprising carrying out the reaction in the presence of coexisting triphenylphosphine or diethylthiourea.

[81] The method according to [80], wherein the reaction is a reaction in the presence of coexisting triphenylphosphine.

[82] The method according to [80] or [81], wherein the dimethoxybenzyl group is a 2,3-dimethoxybenzyl group, a 2,4-dimethoxybenzyl group, a 2,5-dimethoxybenzyl group, a 2,6-dimethoxybenzyl group, a 3,4-dimethoxybenzyl group, or a 3,5-dimethoxybenzyl group.

[83] The method according to [80] or [81], wherein the dimethoxybenzyl group is a 2,4-dimethoxybenzyl group.

[84] The method according to any one of [80] to [83], wherein the acid is a strong acid.

[85] The method according to any one of [80] to [83], wherein the acid is hydrochloric acid, methanesulfonic acid, trifluoromethanesulfonic acid, benzenesulfonic acid, toluenesulfonic acid, or trifluoroacetic acid.

[86] The method according to any one of [80] to [83], wherein the acid is hydrochloric acid.

[87] The method according to any one of [80] to [86], wherein the nitrogen atom to which the dimethoxybenzyl group is bonded is a nitrogen atom constituting a sulfonamide group of a benzenesulfonamide compound.

[88] The method according to [87], wherein the benzenesulfonamide compound is a benzenesulfonamide compound having a substituent(s) on its benzene ring, wherein an aromatic group optionally having a substituent(s) is further bonded to the nitrogen atom of the sulfonamide group to which the dimethoxybenzyl group is bonded.

[89] The method according to [88], wherein the benzenesulfonamide compound is
5-chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide,
5-chloro-N-(2,4-dimethoxybenzyl)-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide,
5-chloro-N-(2,4-dimethoxybenzyl)-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide, 5-chloro-N-(2,4-dimethoxybenzyl)-2-fluoro-4-{[(1S,2R, 5S)-5-hydroxy-2-(1-methyl-1H-pyrazol-5-yl)cyclohexyl]oxy}-N-(pyrimidin-4-yl)benzenesulfonamide,
4-{[(3R,4S)-4-(4-chlorophenyl)piperidin-3-yl]methoxy}-2,5-difluoro-N-(2,4-dimethoxybenzyl)-N-(5-fluoropyrimidin-2-yl)benzenesulfonamide, or
3-cyano-N-(2,4-dimethoxybenzyl)-4-[2-(2-methylpyrazol-3-yl)phenoxy]-N-thiazol-2-yl-benzenesulfonamide.

[90] The method according to [88], wherein the benzenesulfonamide compound is
5-chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide,
5-chloro-N-(2,4-dimethoxybenzyl)-2-fluoro-4-{[(1S,2R, 4R)-4-hydroxy-2-(1-methyl-1H-pyrazol-5-yl)cyclohexyl]oxy}-N-(pyrimidin-4-yl)benzenesulfonamide,
5-chloro-N-(2,4-dimethoxybenzyl)-2-fluoro-4-{[(1S,2R, 4S)-4-hydroxy-2-(1-methyl-1H-pyrazol-5-yl)cyclohexyl]oxy}-N-(pyrimidin-4-yl)benzenesulfonamide, or
5-chloro-N-(2,4-dimethoxybenzyl)-2-fluoro-4-{[(1S,2R, 5S)-5-hydroxy-2-(1-methyl-1H-pyrazol-5-yl)cyclohexyl]oxy}-N-(pyrimidin-4-yl)benzenesulfonamide.

Advantageous Effects of Invention

According to the method of the present invention, in a removal reaction of a dimethoxybenzyl group by acid treatment from a compound containing a dimethoxybenzyl group bonded to a nitrogen atom, in particular, a compound containing a dimethoxybenzyl group bonded to a nitrogen atom constituting a sulfonamide group, a de-dimethoxybenzylated compound can be obtained without forming contaminants that are poorly soluble in both organic solvents and aqueous solvents, and the objective de-dimethoxybenzylated compound can be conveniently obtained at high yields with excellent quality.

DESCRIPTION OF EMBODIMENTS

Figure 1:
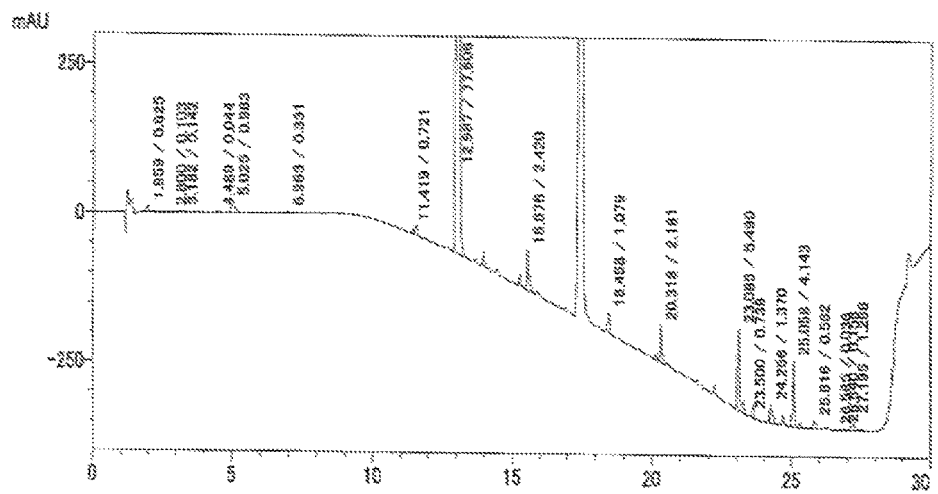
FIG. 1 is a HPLC chart of a reaction solution when 5-chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide was treated with hydrochloric acid in the absence of triphenylphosphine. The abscissa shows time (min).

The present invention will now be described in detail.

A feature of the present invention is that in a removal reaction of a dimethoxybenzyl group by treatment under acidic conditions from a compound containing a dimethoxybenzyl group bonded to a nitrogen atom, the reaction is carried out in the presence of coexisting triphenylphosphine or diethylthiourea. This method can suppress the formation of a poorly soluble product or a poorly soluble by-product considered to result from, for example, the polymerization of a fragment of the cleaved dimethoxybenzyl group. This method can produce a product excellent in quality at high yields by the removal of a dimethoxybenzyl group without complex operation and is therefore excellent as an industrial production method.

The triphenylphosphine or the diethylthiourea that is allowed to coexist with an acid in the method of the present invention has the effect of suppressing the formation of a poorly soluble product. However, the cleavage itself of a dimethoxybenzyl group proceeds at high yields even in the absence of these substances, suggesting no direct involvement thereof in the cleavage of a dimethoxybenzyl group. Specifically, since the poorly soluble product is considered to be formed from a degraded fragment of the dimethoxybenzyl group, the effects brought about by the method of the present invention can be expected, regardless of the type of compound, by the removal of a dimethoxybenzyl group under acidic conditions.

The dimethoxybenzyl group can be any benzyl group in which two methoxy groups are bonded to the phenyl group of the benzyl group, and is not particularly limited by the binding positions of the methoxy groups. Examples thereof can include a 2,3-dimethoxybenzyl group, a 2,4-dimethoxybenzyl group, a 2,5-dimethoxybenzyl group, a 2,6-dimethoxybenzyl group, a 3,4-dimethoxybenzyl group, and a 3,5-dimethoxybenzyl group. Excellent effects are expected on the 2,4-dimethoxybenzyl group.

The nitrogen atom to which the dimethoxybenzyl group is bonded is not particularly limited. In particular, a nitrogen atom constituting a sulfonamide group is preferable, and the effects of the method of the present invention thereon are expected.

Such a sulfonamide group can be any sulfonamide group in which an aromatic group is bonded to the sulfur atom. Such an aromatic group may be an aromatic hydrocarbon group or an aromatic heterocyclic group. Among them, an aromatic hydrocarbon group is more preferable. Preferable examples of the compound to which the method of the present invention can be applied can include aromatic hydrocarbon sulfonamide compounds.

Examples of the aromatic hydrocarbon group can include a phenyl group and a naphthyl group. Among them, a phenyl group is preferable. Thus, the method of the present invention can be preferably applied to a benzenesulfonamide compound.

This aromatic hydrocarbon group may further have a substituent(s) and may be substituted by a halogen atom, an alkyl group, an alkoxy group, a cycloalkyloxy group, a substituted cycloalkyloxy group, a cycloalkyloxymethyl group, a substituted cycloalkyloxymethyl group, a phenyl group, a phenoxy group, a phenoxymethyl group or the like.

The benzenesulfonamide compound can be selected from the group consisting of, for example, 2-fluorobenzenesulfonamide, 2-chlorobenzenesulfonamide, 3-fluorobenzenesulfonamide, 3-chlorobenzenesulfonamide, 2,3-difluorobenzenesulfonamide, 2,3-dichlorobenzenesulfonamide, 2,5-difluorobenzenesulfonamide, 2,5-dichlorobenzenesulfonamide, 2,6-difluorobenzenesulfonamide, 2,6-dichlorobenzenesulfonamide, 2-chloro-5-fluorobenzenesulfonamide, 5-chloro-2-fluorobenzenesulfonamide, 2-fluoro-3-methylbenzenesulfonamide, 2-chloro-3-methylbenzenesulfonamide, 2-fluoro-5-methylbenzenesulfonamide and 2-chloro-5-methylbenzenesulfonamide.

These benzenesulfonamide compounds may further have a substituent(s) on their benzene rings and preferably have a substituent, for example, at the 4-position (para position of the sulfonamide group). Examples of benzenesulfonamide compounds having a halogen atom, particularly, a fluorine atom, at the 4-position can include 2,4-difluorobenzenesulfonamide, 2-chloro-4-fluorobenzenesulfonamide, 3,4-difluorobenzenesulfonamide, 3-chloro-4-fluorobenzenesulfonamide, 2,3,4-trifluorobenzenesulfonamide, 2,3-dichloro-4-fluorobenzenesulfonamide, 2,4,5-trifluorobenzenesulfonamide, 2,5-dichloro-4-fluorobenzenesulfonamide, 2,4,6-trifluorobenzenesulfonamide, 2,6-dichloro-4-fluorobenzenesulfonamide, 2-chloro-4,5-difluorobenzenesulfonamide, 5-chloro-2,4-difluorobenzenesulfonamide, 2,4-difluoro-3-methylbenzenesulfonamide, 2-chloro-4-fluoro-3-methylbenzenesulfonamide, 2,4-difluoro-5-methylbenzenesulfonamide, and 2-chloro-4-fluoro-5-methylbenzenesulfonamide.

Examples of the substituent(s) (corresponding to $R^3$ in a structural formula given below) other than a halogen atom at the 4-position of the benzene ring can include a group having a structure represented by the following formula:

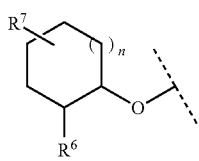

[Formula 20]

Specifically, this group is bonded to the benzene ring via an oxygen atom and has an aromatic group represented by $R^6$ on the carbon atom adjacent to the carbon atom on cycloalkane to which the oxygen atom is bonded. This moiety to which $R^6$ and the oxygen atom are bonded is 1,2-di-substituted, and stereoisomerism occurs due to this moiety. The stereoisomerism is preferably a trans form and is indicated by (1S*,2R*) and more preferably (1S,2R) (see the following structural formula; here, the binding site to the oxygen atom is the 1-position, and the binding site to $R^6$ is the 2-position).

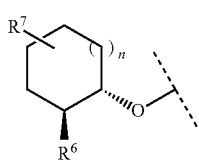

[Formula 21]

In the group represented by the structural formula described above, n is an integer of 0, 1, or 2, and the cyclo ring can be a 5-membered ring, a 6-membered ring, or a 7-membered ring. Among them, a cyclohexyl group having a 6-membered ring is preferable.

$R^6$ can be any aromatic group optionally having a substituent(s). Examples of such an aromatic group can include an aromatic hydrocarbon group and an aromatic heterocyclic group. The aromatic hydrocarbon group can be a phenyl group or a naphthyl group and is preferably a phenyl group. The aromatic heterocyclic group can be any 5-membered ring or 6-membered ring containing 1 to 3 heteroatoms selected from nitrogen, oxygen, and sulfur (s) as heteroatoms. Examples of such an aromatic heterocyclic group can include a pyrrolyl group, a pyrazolyl group, an imidazolyl group, a thiazolyl group, a thiadiazolyl group, a pyridyl group, a pyridazinyl group, a pyrimidyl group and a pyrazyl group. Among them, an aromatic heterocyclic group having a nitrogen atom as a heteroatom is preferable, and a pyrazolyl group, an imidazolyl group, a pyridyl group or a pyridazinyl group is preferable. Specific examples thereof can include a 1H-pyrazol-4-yl group, a 1H-pyrazol-5-yl group, 1H-imidazol-1-yl group, a pyridin-4-yl group, a pyridin-3-yl group and a pyridazin-4-yl group. Among them, a 1H-pyrazol-4-yl group or a 1H-pyrazol-5-yl group is preferable.

Examples of the substituent(s) on the substituent $R^6$ can include an alkyl group having a carbon number of 1 to 6, a halogen atom and an amino group. Examples of the alkyl group having a carbon number of 1 to 6 can include a methyl group and an ethyl group. The halogen atom can be a fluorine atom or a chlorine atom. $R^6$ can be substituted by 1 to 3 substituents, and two or more substituents may be the same as or different from each other.

A substituent(s) other than $R^6$ may be present on the cyclo ring. The cyclo ring may be substituted by, for example, a hydroxyl group, a halogen atom or an alkyl group having a carbon number of 1 to 6. Such a substituent is preferably a fluorine atom as the halogen atom and a methyl group as the alkyl group having a carbon number of 1 to 6. Preferably, one carbon atom is substituted by two fluorine atoms. The substituent $R^7$, which is a substituent(s) other than $R^6$, is more preferably a hydrogen atom, a hydroxyl group, or one or two halogen atoms. When the substituent $R^7$ is two halogen atoms, the substitution positions may be the same carbon atom or may be different carbon atoms. Examples of the structure substituted by a hydroxyl group can include the following:

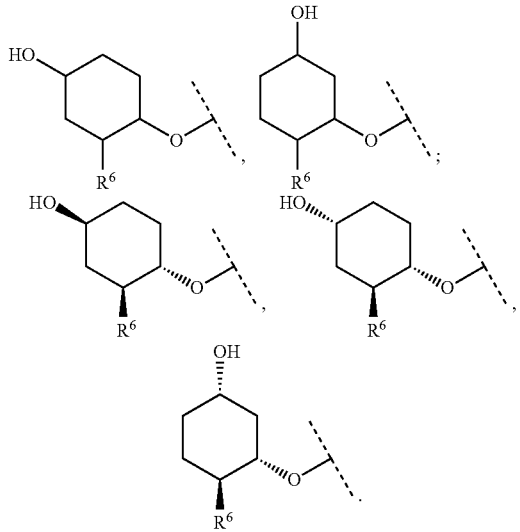

[Formula 22]

The hydroxyl group on the cyclo ring is not stereoinverted by treatment under reaction conditions for the removal reaction of a dimethoxybenzyl group of the present invention.

Preferable examples of the substituent at the 4-position of the benzene ring of the benzenesulfonamide compound can include the following:

a 2-(1H-pyrazol-5-yl)cyclopentyloxy group,
a 2-(1H-pyrazol-4-yl)cyclohexyloxy group,
a 2-(1H-pyrazol-4-yl)cycloheptyloxy group,
a 2-(1-methyl-1H-pyrazol-5-yl)cyclopentyloxy group,
a 2-(1-methyl-1H-pyrazol-5-yl)cyclohexyloxy group,
a 2-(1-methyl-1H-pyrazol-5-yl)cycloheptyloxy group,
a 2-(1-ethyl-1H-pyrazol-5-yl)cyclopentyloxy group,
a 2-(1-ethyl-1H-pyrazol-5-yl)cyclohexyloxy group,
a 2-(1-ethyl-1H-pyrazol-5-yl)cycloheptyloxy group,
a 4,4-difluoro-2-(1H-pyrazol-4-yl)cyclopentyloxy group,
a 5,5-difluoro-2-(1H-pyrazol-4-yl)cyclohexyloxy group,
a 6,6-difluoro-2-(1H-pyrazol-4-yl)cycloheptyloxy group,
a 4,4-difluoro-2-(1-methyl-1H-pyrazol-5-yl)cyclopentyloxy group,
a 5,5-difluoro-2-(1-methyl-1H-pyrazol-5-yl)cyclohexyloxy group,
a 6,6-difluoro-2-(1-methyl-1H-pyrazol-5-yl)cycloheptyloxy group,
a 4-hydroxy-2-(1-methyl-1H-pyrazol-5-yl)cyclohexyloxy group,
a 5-hydroxy-2-(1-methyl-1H-pyrazol-5-yl)cyclohexyloxy group,
a 2-(3-amino-1H-pyrazol-4-yl)cyclopentyloxy group,
a 2-(3-amino-1H-pyrazol-4-yl)cyclohexyloxy group, and
a 2-(3-amino-1H-pyrazol-4-yl)cycloheptyloxy group.

Among them, a (1S*,2R*) form is preferable, and a (1S,2R) form is more preferable (here, the binding site to the oxygen atom is the 1-position, and the binding site to $R^6$ is the 2-position).

Among them, the following is preferable:
a (1S*,2R*)-2-(1H-pyrazol-5-yl)cyclopentyloxy group,
a (1S*,2R*)-2-(1H-pyrazol-4-yl)cyclohexyloxy group,
a (1S*,2R*)-2-(1-methyl-1H-pyrazol-5-yl)cyclopentyloxy group,
a (1S*,2R*)-2-(1-methyl-1H-pyrazol-5-yl)cyclohexyloxy group,
a (1S*,2R*)-2-(1-ethyl-1H-pyrazol-5-yl)cyclopentyloxy group,
a (1S*,2R*)-5,5-difluoro-2-(1-methyl-1H-pyrazol-5-yl)cyclohexyloxy group,
a (1S,2R,4R)-4-hydroxy-2-(1-methyl-1H-pyrazol-5-yl)cyclohexyloxy group,
a (1S,2R,4S)-4-hydroxy-2-(1-methyl-1H-pyrazol-5-yl)cyclohexyloxy group,
a (1S,2R,5S)-5-hydroxy-2-(1-methyl-1H-pyrazol-5-yl)cyclohexyloxy group,
a (1S,2R)-2-(1H-pyrazol-5-yl)cyclopentyloxy group,
a (1S,2R)-2-(1H-pyrazol-4-yl)cyclohexyloxy group,
a (1S,2R)-2-(1-methyl-1H-pyrazol-5-yl)cyclopentyloxy group,
a (1S,2R)-2-(1-methyl-1H-pyrazol-5-yl)cyclohexyloxy group,
a (1S,2R)-2-(1-ethyl-1H-pyrazol-5-yl)cyclopentyloxy group,
a (1S,2R)-5,5-difluoro-2-(1-methyl-1H-pyrazol-5-yl)cyclohexyloxy group,
a (1S,2R,4R)-4-hydroxy-2-(1-methyl-1H-pyrazol-5-yl)cyclohexyloxy group,
a (1S,2R,4S)-4-hydroxy-2-(1-methyl-1H-pyrazol-5-yl)cyclohexyloxy group, or
a (1S,2R,5S)-5-hydroxy-2-(1-methyl-1H-pyrazol-5-yl)cyclohexyloxy group.

The following is more preferable:
a (1S*,2R*)-2-(1H-pyrazol-4-yl)cyclohexyloxy group,
a (1S*,2R*)-2-(1-methyl-1H-pyrazol-5-yl)cyclopentyloxy group,
a (1S*,2R*)-2-(1-methyl-1H-pyrazol-5-yl)cyclohexyloxy group,
a (1S,2R)-2-(1-ethyl-1H-pyrazol-5-yl)cyclopentyloxy group,
a (1S,2R)-2-(1-methyl-1H-pyrazol-5-yl)cyclohexyloxy group,
a (1S*,2R*)-5,5-difluoro-2-(1H-pyrazol-4-yl)cyclohexyloxy group,
a (1S,2R)-5,5-difluoro-2-(1H-pyrazol-4-yl)cyclohexyloxy group,
a (1S,2R,4R)-4-hydroxy-2-(1-methyl-1H-pyrazol-5-yl)cyclohexyloxy group,
a (1S,2R,4S)-4-hydroxy-2-(1-methyl-1H-pyrazol-5-yl)cyclohexyloxy group, or
a (1S,2R,5S)-5-hydroxy-2-(1-methyl-1H-pyrazol-5-yl)cyclohexyloxy group.

Alternatively, the substituent (corresponding to $R^3$ in a structural formula given below) at the 4-position of the benzene ring of the benzenesulfonamide compound may be a group having a structure represented by the following formula:

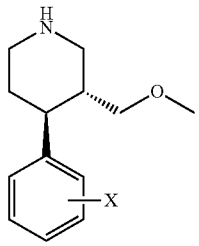

[Formula 23]

in which the oxygen atom of the methyleneoxy is the binding site to the benzene ring of benzenesulfonamide.

In the formula, X represents 1 or 2 groups selected from the group consisting of a hydrogen atom, a fluorine atom, a chlorine atom and a methyl group.

Examples of X in this group can include a hydrogen atom and substitution patterns such as 4-fluorine atom substitution, 4-chlorine atom substitution, 3,4-difluorine atom substitution, 3-fluorine atom-4-chlorine atom substitution, and 4-methyl group substitution. Among them, 4-fluorine atom substitution or 4-chlorine atom substitution is preferable, and 4-chlorine atom substitution is more preferable. Here, the carbon atom of the benzene ring bonded to the piperidine ring is the 1-position.

In this substituent, the methyleneoxy and the phenyl group establish 1,2-di-substitution, resulting in stereoisomerism. However, the conformation described above is preferable.

The benzene ring of the benzenesulfonamide compound having the substituent described above may further have a substituent(s). The substituent(s) can be any of those listed above and can be 1 or 2 groups selected from the group consisting of a methyl group, an ethyl group, a fluorine atom and a chlorine atom. The two substituents may be the same as or different from each other. This substituent(s) is preferably a fluorine atom and more preferably 2,5-difluoro.

The substituent (corresponding to $R^a$ in a structural formula given below) optionally having a substituent(s), on the nitrogen atom constituting a sulfonamide group of the benzenesulfonamide compound having the substituent described above can be any aromatic group and may be a thiazolyl group, a thiadiazolyl group, an oxazolyl group, a pyridyl group, a pyridazinyl group or a pyrimidyl group. Specific examples thereof can include a 1,3-thiazol-2-yl group, a 1,2-oxazol-3-yl group, a 1,2,4-thiadiazol-5-yl group, a 1,3,4-thiadiazol-2-yl group, a pyridin-2-yl group, a pyridazin-3-yl group, a pyrimidin-2-yl group and a pyrimidin-4-yl group. These groups may also have a substituent(s) and may have 1 or 2 groups selected from the group consisting of a methyl group, an ethyl group, a fluorine atom and a chlorine atom. The two substituents may be the same as or different from each other. $R^a$ having the substituent(s) described above is preferably an aromatic group such as a 5-methyl-1,3-thiazol-2-yl group, a 5-chloro-1,3-thiazol-2-yl group, a 1,3,4-thiadiazol-2-yl group, a 5-fluoro-pyridin-2-yl group, a pyridazin-3-yl group, a pyrimidin-2-yl group, a 5-fluoro-pyrimidin-2-yl group or a pyrimidin-4-yl group. Among them, a 5-fluoro-pyrimidin-2-yl group is preferable.

An aromatic group (corresponding to $R^a$ in a structural formula given below) may be further bonded to the nitrogen atom of the sulfonamide group to which the dimethoxybenzyl group is bonded. Such an aromatic group can be an aromatic hydrocarbon group or an aromatic heterocyclic group. Examples of the aromatic hydrocarbon group can include a phenyl group and a naphthyl group. A phenyl group is more preferable.

The aromatic heterocyclic group can contain nitrogen, oxygen or sulfur atom(s) as heteroatom(s) and can be any 5-membered ring or 6-membered ring containing 1 or 3 heteroatoms selected from nitrogen, oxygen, and sulfur atom(s) as heteroatoms. Examples of such an aromatic heterocyclic group can include a pyrrolyl group, a pyrazolyl group, an imidazolyl group, a thiazolyl group, a thiadiazolyl group, a pyridyl group, a pyridazinyl group, a pyrimidyl group and a pyrazyl group. Among them, a thiazolyl group, a thiadiazolyl group or a pyrimidyl group can be used. Specific examples thereof can include a thiadiazolyl-5-yl group, a thiazolyl-4-yl group, a thiazolyl-2-yl group and a pyrimidyl-4-yl group.

The second aromatic hydrocarbon group or aromatic heterocyclic group (corresponding to $R^a$ in a structural formula given below) on the nitrogen atom of this sulfonamide group may have a substituent(s) and may be substituted by a halogen atom, an alkyl group or the like. More specifically, this group may be substituted by 1 to 3 groups selected from a fluorine atom, a chlorine atom, a methyl group and an ethyl group. Two or more substituents may be the same as or different from each other.

Examples of the compound to which the method of the present invention can be applied can include a compound represented by the following formula:

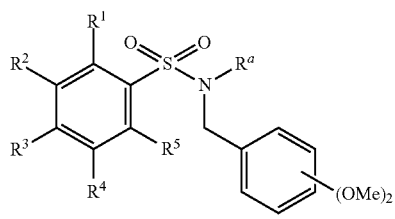

[Formula 24]

wherein —(OMe)$_2$ represents that the benzene ring is substituted by two methoxy groups.

This compound is more preferably a compound represented by the following formula:

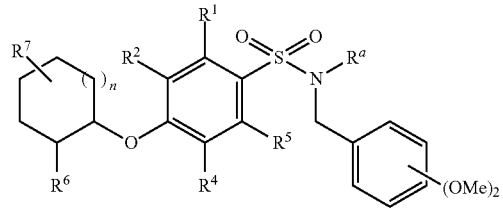

[Formula 25]

From this compound, the dimethoxybenzyl group is removed by using the method of the present invention to preferably produce a compound represented by the following formula:

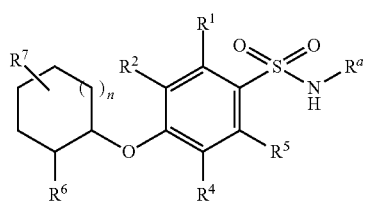

[Formula 26]

Examples of such a de-dimethoxybenzyl compound can include a compound selected from the group given below. The production of these compounds is described in Patent Literature 4. These compounds are produced by the removal of a 2,4-dimethoxybenzyl group from a benzenesulfonamide compound containing a 2,4-dimethoxybenzyl group bonded to the nitrogen atom of the sulfonamide group.

2,5-Difluoro-4-{[ (1S*,2R*)-2-(1-methyl-1H-pyrazol-5-yl)cyclopentyl]oxy}-N-(pyrimidin-4-yl)benzenesulfonamide, 2,5-difluoro-4-{[ (1S*,2R*)-2-(1-methyl-1H-pyrazol-5-yl)cyclopentyl]oxy}-N-(1,3-thiazol-2-yl)benzenesulfonamide, 3-chloro-4-{[ (1S*,2R*)-2-(1-methyl-1H-pyrazol-5-yl)cyclopentyl]oxy}-N-(pyrimidin-4-yl)benzenesulfonamide, 2,5-difluoro-4-{[ (1S*,2R*)-2-(1-methyl-1H-pyrazol-5-yl)cyclohexyl]oxy}-N-(pyrimidin-4-yl)benzenesulfonamide, 2-fluoro-4-{[ (1S*,2R*)-2-(1-methyl-1H-pyrazol-5-yl)cyclopentyl]oxy}-N-(pyrimidin-4-yl)benzenesulfonamide, 2,5-difluoro-4-{[ (1S,2R)-2-(1-methyl-1H-pyrazol-5-yl)cyclopentyl]oxy}-N-(pyrimidin-4-yl)benzenesulfonamide, 2,5-difluoro-4-{[(1S*,2R*)-2-(1H-pyrazol-4-yl)cyclohexyl]oxy}-N-(pyrimidin-4-yl)benzenesulfonamide, 4-{[ (1S*,2R*)-2-(1-ethyl-1H-pyrazol-5-yl)cyclopentyl]oxy}-2,3-difluoro-N-(pyrimidin-4-yl)benzenesulfonamide, 2,3-difluoro-4-{[ (1S*,2R*)-2-(1-methyl-1H-pyrazol-5-yl)cyclohexyl]oxy}-N-(pyrimidin-4-yl)benzenesulfonamide, 4-{[ (1S*,2R*)-5,5-difluoro-2-(1-methyl-1H-pyrazol-5-yl)cyclohexyl]oxy}-2,5-difluoro-N-(pyrimidin-4-yl)benzenesulfonamide, 5-chloro-2-fluoro-4-{[ (1S*,2R*)-2-(1-methyl-1H-pyrazol-5-yl)cyclohexyl]oxy}-N-(pyrimidin-4-yl)benzenesulfonamide, 2-fluoro-4-{[(1S*,2R*)-2-(1-methyl-1H-pyrazol-5-yl)cycloheptyl]oxy}-N-(pyrimidin-4-yl)benzenesulfonamide, 2-fluoro-3-methyl-4-{[(1S*,2R*)-2-(1-methyl-1H-pyrazol-5-yl)cyclohexyl]oxy}-N-(pyrimidin-4-yl)benzenesulfonamide,
4-{[(1S*,2R*)-2-(3-amino-1H-pyrazol-4-yl)cyclohexyl]oxy}-2-fluoro-5-methyl-N-(pyrimidin-4-yl)benzenesulfonamide,
4-{[(1S*,2R*)-2-(3-amino-1H-pyrazol-4-yl)cyclohexyl]oxy}-5-chloro-2-fluoro-N-(pyrimidin-4-yl)benzenesulfonamide,
4-{[(1S*,2R*)-2-(3-amino-1H-pyrazol-4-yl)cyclohexyl]oxy}-2-fluoro-3-methyl-N-(pyrimidin-4-yl)benzenesulfonamide,
2,6-difluoro-4-{[(1S*,2R*)-2-(1H-pyrazol-4-yl)cyclohexyl]oxy}-N-(pyrimidin-4-yl)benzenesulfonamide,
4-{[(1S,2R)-5,5-difluoro-2-(1-methyl-1H-pyrazol-5-yl)cyclohexyl]oxy}-2,5-difluoro-N-(pyrimidin-4-yl)benzenesulfonamide,
4-{[(1S,2R)-2-(1-ethyl-1H-pyrazol-5-yl)cyclopentyl]oxy}-2,3-difluoro-N-(pyrimidin-4-yl)benzenesulfonamide,
5-chloro-2-fluoro-4-{[(1S,2R)-2-(1-methyl-1H-pyrazol-5-yl)cyclohexyl]oxy}-N-(pyrimidin-4-yl)benzenesulfonamide,
2-fluoro-4-{[(1S,2R)-2-(1-methyl-1H-pyrazol-5-yl)cyclopentyl]oxy}-N-(pyrimidin-4-yl)benzenesulfonamide,
4-{[(1S*,2R*)-5,5-difluoro-2-(1H-pyrazol-4-yl)cyclohexyl]oxy}-2-fluoro-5-methyl-N-(pyrimidin-4-yl)benzenesulfonamide,
4-{[(1S*,2R*)-4,4-difluoro-2-(1-methyl-1H-pyrazol-5-yl)cyclopentyl]oxy}-2-fluoro-5-methyl-N-(pyrimidin-4-yl)benzenesulfonamide,
4-{[(1S*,2R*)-5,5-difluoro-2-(1-methyl-1H-pyrazol-5-yl)cyclohexyl]oxy}-2-fluoro-5-methyl-N-(pyrimidin-4-yl)benzenesulfonamide,
2-fluoro-5-methyl-4-{[(1S*,2R*)-2-(1H-pyrazol-5-yl)cyclopentyl]oxy}-N-(pyrimidin-4-yl)benzenesulfonamide,
5-chloro-2-fluoro-4-{[(1S*,2R*)-2-(1H-pyrazol-5-yl)cyclopentyl]oxy}-N-(pyrimidin-4-yl)benzenesulfonamide,
4-{[(1S,2R)-5,5-difluoro-2-(1H-pyrazol-4-yl)cyclohexyl]oxy}-2-fluoro-5-methyl-N-(pyrimidin-4-yl)benzenesulfonamide,
2-fluoro-5-methyl-4-{[(1S,2R)-2-(1H-pyrazol-5-yl)cyclopentyl]oxy}-N-(pyrimidin-4-yl)benzenesulfonamide,
5-chloro-2-fluoro-4-{[(1S,2R)-2-(1H-pyrazol-5-yl)cyclopentyl]oxy}-N-(pyrimidin-4-yl)benzenesulfonamide,
5-chloro-4-{[(1S*,2R*)-5,5-difluoro-2-(1H-pyrazol-4-yl)cyclohexyl]oxy}-2-fluoro-N-(pyrimidin-4-yl)benzenesulfonamide,
2,6-difluoro-4-{[(1S,2R)-2-(1H-pyrazol-4-yl)cyclohexyl]oxy}-N-(pyrimidin-4-yl)benzenesulfonamide,
5-chloro-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide,
5-chloro-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide, and
5-chloro-2-fluoro-4-{[(1S,2R,5S)-5-hydroxy-2-(1-methyl-1H-pyrazol-5-yl)cyclohexyl]oxy}-N-(pyrimidin-4-yl)benzenesulfonamide.

A compound selected from the following group is more preferable:
2-fluoro-4-{[(1S*,2R*)-2-(1-methyl-1H-pyrazol-5-yl)cyclopentyl]oxy}-N-(pyrimidin-4-yl)benzenesulfonamide,
2,5-difluoro-4-{[(1S*,2R*)-2-(1H-pyrazol-4-yl)cyclohexyl]oxy}-N-(pyrimidin-4-yl)benzenesulfonamide,
4-{[(1S*,2R*)-2-(1-ethyl-1H-pyrazol-5-yl)cyclopentyl]oxy}-2,3-difluoro-N-(pyrimidin-4-yl)benzenesulfonamide,
4-{[(1S*,2R*)-5,5-difluoro-2-(1-methyl-1H-pyrazol-5-yl)cyclohexyl]oxy}-2,5-difluoro-N-(pyrimidin-4-yl)benzenesulfonamide,
5-chloro-2-fluoro-4-{[(1S*,2R*)-2-(1-methyl-1H-pyrazol-5-yl)cyclohexyl]oxy}-N-(pyrimidin-4-yl)benzenesulfonamide,
2,6-difluoro-4-{[(1S*,2R*)-2-(1H-pyrazol-4-yl)cyclohexyl]oxy}-N-(pyrimidin-4-yl)benzenesulfonamide,
4-{[(1S,2R)-5,5-difluoro-2-(1-methyl-1H-pyrazol-5-yl)cyclohexyl]oxy}-2,5-difluoro-N-(pyrimidin-4-yl)benzenesulfonamide,
4-{[(1S,2R)-2-(1-ethyl-1H-pyrazol-5-yl)cyclopentyl]oxy}-2,3-difluoro-N-(pyrimidin-4-yl)benzenesulfonamide,
5-chloro-2-fluoro-4-{[(1S,2R)-2-(1-methyl-1H-pyrazol-5-yl)cyclohexyl]oxy}-N-(pyrimidin-4-yl)benzenesulfonamide,
2-fluoro-4-{[(1S,2R)-2-(1-methyl-1H-pyrazol-5-yl)cyclopentyl]oxy}-N-(pyrimidin-4-yl)benzenesulfonamide,
4-{[(1S*,2R*)-5,5-difluoro-2-(1H-pyrazol-4-yl)cyclohexyl]oxy}-2-fluoro-5-methyl-N-(pyrimidin-4-yl)benzenesulfonamide,
2-fluoro-5-methyl-4-{[(1S*,2R*)-2-(1H-pyrazol-5-yl)cyclopentyl]oxy}-N-(pyrimidin-4-yl)benzenesulfonamide,
5-chloro-2-fluoro-4-{[(1S*,2R*)-2-(1H-pyrazol-5-yl)cyclopentyl]oxy}-N-(pyrimidin-4-yl)benzenesulfonamide,
4-{[(1S,2R)-5,5-difluoro-2-(1H-pyrazol-4-yl)cyclohexyl]oxy}-2-fluoro-5-methyl-N-(pyrimidin-4-yl)benzenesulfonamide,
2-fluoro-5-methyl-4-{[(1S,2R)-2-(1H-pyrazol-5-yl)cyclopentyl]oxy}-N-(pyrimidin-4-yl)benzenesulfonamide,
2,6-difluoro-4-{[(1S,2R)-2-(1H-pyrazol-4-yl)cyclohexyl]oxy}-N-(pyrimidin-4-yl)benzenesulfonamide,
5-chloro-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide,
5-chloro-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide, and
5-chloro-2-fluoro-4-{[(1S,2R,5S)-5-hydroxy-2-(1-methyl-1H-pyrazol-5-yl)cyclohexyl]oxy}-N-(pyrimidin-4-yl)benzenesulfonamide.

A compound selected from the following group is further preferable:
2-fluoro-4-{[(1S*,2R*)-2-(1-methyl-1H-pyrazol-5-yl)cyclopentyl]oxy}-N-(pyrimidin-4-yl)benzenesulfonamide,
4-{[(1S*,2R*)-2-(1-ethyl-1H-pyrazol-5-yl)cyclopentyl]oxy}-2,3-difluoro-N-(pyrimidin-4-yl)benzenesulfonamide,
5-chloro-2-fluoro-4-{[(1S*,2R*)-2-(1-methyl-1H-pyrazol-5-yl)cyclohexyl]oxy}-N-(pyrimidin-4-yl)benzenesulfonamide,
2,6-difluoro-4-{[(1S*,2R*)-2-(1H-pyrazol-4-yl)cyclohexyl]oxy}-N-(pyrimidin-4-yl)benzenesulfonamide,
4-{[(1S,2R)-2-(1-ethyl-1H-pyrazol-5-yl)cyclopentyl]oxy}-2,3-difluoro-N-(pyrimidin-4-yl)benzenesulfonamide,
5-chloro-2-fluoro-4-{[(1S,2R)-2-(1-methyl-1H-pyrazol-5-yl)cyclohexyl]oxy}-N-(pyrimidin-4-yl)benzenesulfonamide,
2-fluoro-4-{[(1S,2R)-2-(1-methyl-1H-pyrazol-5-yl)cyclopentyl]oxy}-N-(pyrimidin-4-yl)benzenesulfonamide,
4-{[(1S*,2R*)-5,5-difluoro-2-(1H-pyrazol-4-yl)cyclohexyl]oxy}-2-fluoro-5-methyl-N-(pyrimidin-4-yl)benzenesulfonamide,
4-{[(1S,2R)-5,5-difluoro-2-(1H-pyrazol-4-yl)cyclohexyl]oxy}-2-fluoro-5-methyl-N-(pyrimidin-4-yl)benzenesulfonamide, 2,6-difluoro-4-{[(1S,2R)-2-(1H-pyrazol-4-yl)cyclohexyl]
oxy}-N-(pyrimidin-4-yl)benzenesulfonamide, 5-chloro-2-fluoro-4-{[(1S,2R,4R)-4-hydroxy-2-(1-methyl-
1H-pyrazol-5-yl)cyclohexyl]oxy}-N-(pyrimidin-4-yl)
benzenesulfonamide, 5-chloro-2-fluoro-4-{[(1S,2R,4S)-4-hydroxy-2-(1-methyl-
1H-pyrazol-5-yl)cyclohexyl]oxy}-N-(pyrimidin-4-yl)
benzenesulfonamide, and 5-chloro-2-fluoro-4-{[(1S,2R,5S)-5-hydroxy-2-(1-methyl-
1H-pyrazol-5-yl)cyclohexyl]oxy}-N-(pyrimidin-4-yl)
benzenesulfonamide.

Furthermore, 4-{[(3R,4S)-4-(4-chlorophenyl)piperidin-3-yl]methoxy}-2,5-difluoro-N-(5-fluoropyrimidin-2-yl)benzenesulfonamide can be preferably produced as the de-dimethoxybenzylated compound. Likewise, 3-cyano-4-[2-(2-methylpyrazol-3-yl)phenoxy]-N-thiazol-2-yl-benzenesulfonamide can be preferably produced as an additional de-dimethoxybenzylated compound.

In the case of a compound having one dimethoxybenzyl group, the triphenylphosphine can be used in an equivalent amount and may be used in a small excess. There is no particular limitation on the execution of the reaction. Usually, the triphenylphosphine and the compound having a dimethoxybenzyl group are dissolved in a reaction solvent. Then, an acid is added to the solution, and the mixture can be reacted at room temperature or by warming, though the procedure is not limited thereto. Also, 1,3-diethyl-2-thiourea can be used instead of triphenylphosphine. Other N,N'-dialkylthioureas can also be used. These substances can be used alone to suppress the formation of a poorly soluble product, but may be used as a mixture.

The method of the present invention can be carried out by using a solvent that does not inhibit the reaction. Such a solvent is not particularly limited as long as the acid for removing a dimethoxybenzyl group can be dissolved in the solvent. For example, when hydrochloric acid is used as the acid, a solvent miscible in water is preferably used. A solvent immiscible in water can be used as a mixed solvent with a solvent miscible in water. The solvent miscible in water is preferably acetonitrile. In addition, a mixed solvent of acetonitrile and toluene, a mixed solvent of methanol and toluene, or the like can be preferably used. In the case of using an organic acid as the acid, these solvents can also be used.

The reaction is carried out in the presence of an acid. This acid can be any acid usually used for the removal of a dimethoxybenzyl group. Such an acid may be an organic acid or an inorganic acid, and any acid classified as a strong acid can be used. An acid having a reduced acidity can be expected to achieve the removal of a dimethoxybenzyl group, for example, by elevating the treatment temperature. However, the treatment temperature is considered to be preferably a lower temperature in terms of the formation of a poorly soluble product. Examples of the inorganic acid for the removal of a dimethoxybenzyl group can include hydrochloric acid and sulfuric acid. Concentrated hydrochloric acid can be preferably used. Sulfonic acids, acetic acids and the like can be used as the organic acid, and methanesulfonic acid, trifluoromethanesulfonic acid, benzenesulfonic acid, toluenesulfonic acid, or trifluoroacetic acid can be preferably used. The concentrated hydrochloric acid is suitable for industrial use in terms of price, easy availability, etc. These acids can be used alone, but may be used as a mixture.

The amount of the acid used can be on the order of 5 to 10 equivalents with respect to a compound having one dimethoxybenzyl group, and can be appropriately increased or decreased depending on the compound to thereby achieve the removal of the dimethoxybenzyl group.

The reaction proceeds even under mild conditions. The de-dimethoxybenzylation reaction can be carried out at a temperature in a range on the order of 20 to 50° C., basically on the order of 40° C., without forming poorly soluble contaminants. The reaction time can be usually on the order of 1 to 6 hours.

Figure 2:
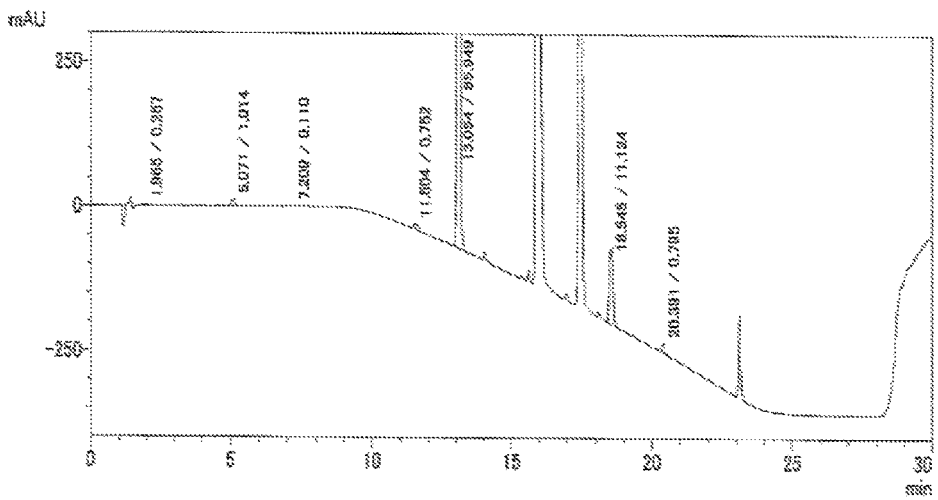
FIG. 2 is a HPLC chart of a reaction solution when 5-chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide was treated with hydrochloric acid in the presence of triphenylphosphine. A plurality of peaks at 21 minutes or later observed in the reaction in the absence of triphenylphosphine (see FIG. 1; here, the peak at 23 minutes is derived from triphenylphosphine and therefore excluded) are not observed, demonstrating the suppression of formation of a poorly soluble product. The abscissa shows time (min).

The poorly soluble product considered to be formed from the removed dimethoxybenzyl group is dissolved, albeit poorly soluble, in a trace amount in the reaction solution. Therefore, the presence thereof can be confirmed by analyzing the reaction solution by HPLC (FIG. 1). In the method of the present invention, a peak based on this poorly soluble product in the reaction solution is not observed, and the suppression of formation of the poorly soluble product can also be confirmed from the analysis of the reaction solution (FIG. 2).

Operation after the reaction can be carried out according to methods usually carried out in this field. Examples thereof can include, but are not limited to, A) a method of cooling the reaction solution to room temperature or lower, then collecting precipitates by filtration, and washing the precipitates with a solvent such as acetonitrile, followed by drying, and B) a method of cooling the reaction solution to room temperature or lower, then concentrating the reaction solution under reduced pressure (partially distilling off acetonitrile), pouring water to the residue, adjusting the pH within the system to approximately 2 to 4 by the addition of an aqueous sodium hydroxide solution, then stirring the mixture, collecting precipitates by filtration, and washing the collected precipitates with a solvent such as aqueous acetonitrile, followed by drying.

The method of the present invention can be preferably used as a method for producing a specific compound, but can be widely applied, in the presence of triphenylphosphine or diethylthiourea in the reaction process under acidic conditions, as, for example, 1. a method for producing a de-dimethoxybenzylated compound, comprising subjecting a compound having a dimethoxybenzyl group bonded to a nitrogen atom to acid treatment to remove the dimethoxybenzyl group, 2. a method for removing a dimethoxybenzyl group bonded to a nitrogen atom, comprising performing treatment in the presence of an acid and in the presence of triphenylphosphine or diethylthiourea, and 3. a method for suppressing the formation of a poorly soluble reaction product in a removal reaction of a dimethoxybenzyl group bonded to a nitrogen atom in the presence of an acid (formation suppression method).

EXAMPLES

The present invention will now be described specifically with reference to examples, but the present invention is not limited to these examples. These should not be restrictively interpreted in any sense. The temperature described for the reaction is the so-called internal temperature and is the temperature of the reaction solution or reaction mixture, unless otherwise specified. The concentration of a solution containing a reagent (particularly, a solid) dissolved therein is indicated by w/v.

Reference Example 1 6-Chloro-N-(2,4-dimethoxy-benzylamino)pyrimidin-4-amine

[Formula 27]

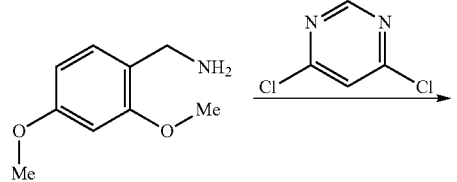

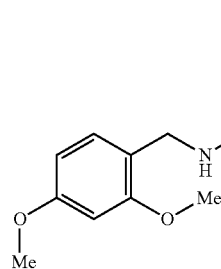

To a solution of 2,4-dimethoxybenzylamine (50.0 g, 0.299 mol) in 2-propanol (225 mL), 4,6-dichloropyrimidine (44.5 g, 0.299 mol) was added at a temperature of 40 to 50° C., then triethylamine (60.5 g, 0.598 mol) was added, and the reaction solution was stirred at approximately 60° C. for approximately 1 hour. The reaction solution was cooled to approximately 40° C. Then, water (450 mL) was slowly added thereto, and the mixture was cooled to approximately 5° C. Then, precipitates were collected by filtration and dried under reduced pressure to obtain the title compound (79.60 g, 95%) as a white solid.

$^1$H-NMR (500 MHz, CDCl$_3$) δ ppm: 3.80 (3H, s), 3.83 (3H, s), 4.40 (1H, br s), 6.37 (1H, br s), 6.44 (1H, dd, J=2.5, 8.0 Hz), 6.48 (2H, d, J=2.5 Hz), 7.15-7.17 (1H, m), 8.30 (1H, br s).

Example 1 5-Chloro-2-fluoro-4-{[(1S,2R)-2-(1-methyl-1H-pyrazol-5-yl)cyclohexyl]oxy}-N-(pyrimidin-4-yl)benzenesulfonamide

[Formula 28]

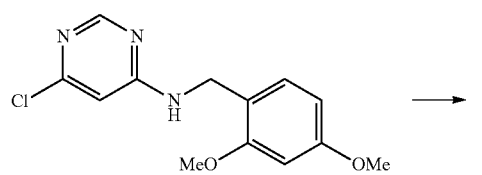

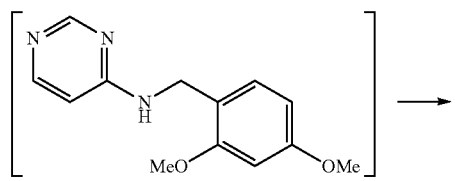

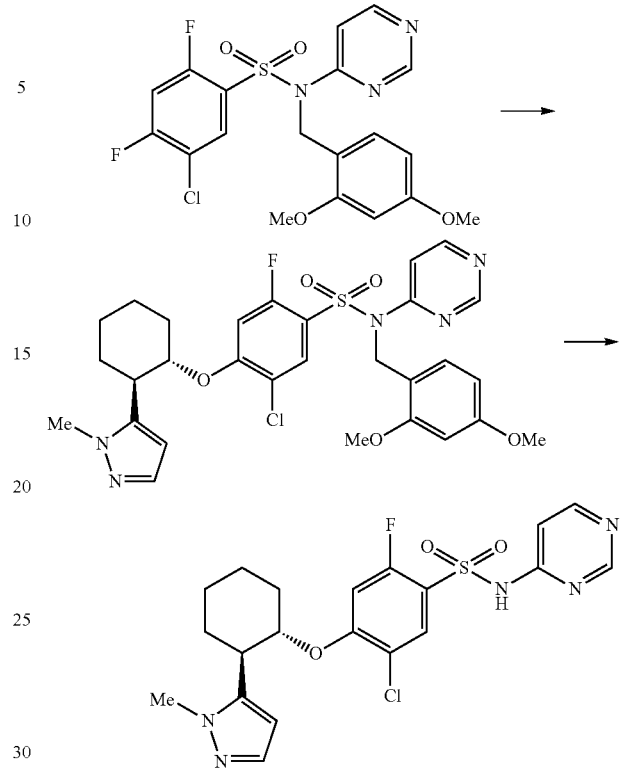

1-1) N-(2,4-Dimethoxybenzyl)pyrimidin-4-amine

A mixture of 6-chloro-N-(2,4-dimethoxybenzyl)pyrimidin-4-amine (40.0 g, 0.143 mol), tetrahydrofuran (hereinafter, referred to as THF; 200 mL), triethylamine (20 mL, 0.143 mol), water (120 mL), and 5% Pd/C (50% wet product, 4.48 g) was stirred for approximately 2.5 hours under conditions involving an internal temperature of 35° C. to 45° C. and a hydrogen pressure of approximately 3 kPa. The internal temperature was lowered to approximately 25° C., and Pd/C was then filtered off and washed with THF (80 mL) and water (40 ml). The filtrate and the washes were combined and concentrated under reduced pressure to bring the amount of the solution to approximately 200 mL. Then, ethyl acetate (200 mL) was added to the residue, and the mixture was stirred for approximately 5 minutes. After separation into an organic layer and an aqueous layer, ethyl acetate (80 mL) was added to the aqueous layer, and the mixture was stirred for approximately 5 minutes. After separation into an organic layer and an aqueous layer, the organic layers were combined. A 20% aqueous sodium chloride solution (40 mL) was added thereto, and the mixture was stirred for approximately 5 minutes. After separation into an organic layer and an aqueous layer, the organic layer was concentrated under reduced pressure to bring the amount of the solution to approximately 120 mL. Then, ethyl acetate (200 mL) was added to the residue, and the mixture was concentrated again under reduced pressure to bring the amount of the solution to approximately 120 mL. Ethyl acetate (120 mL) was further added to the residue, and the mixture was concentrated under reduced pressure to bring the amount of the solution to approximately 120 mL. In this way, a solution of N-(2,4-dimethoxybenzyl)pyrimidin-4-amine in ethyl acetate was obtained.

1-2) 5-Chloro-N-(2,4-dimethoxybenzyl)-2,4-difluoro-N-(pyrimidin-4-yl)benzenesulfonamide To a solution of 5-chloro-2,4-difluorobenzenesulfonyl chloride (45.93 g, 0.186 mol) in ethyl acetate (200 mL), a mixture of the solution of N-(2,4-dimethoxybenzyl)pyrimidin-4-amine in ethyl acetate obtained in Example 1-1), ethyl acetate (200 mL), and 1,4-diazabicyclo[2.2.2]octane (27.27 g, 0.243 mol) was added dropwise with stirring at an internal temperature in the range of 20° C. to 30° C. over approximately 1 hour. After the completion of dropwise addition, the mixture was stirred for approximately 0.5 hours. Subsequently, ethyl acetate (120 mL) and a 5% aqueous sodium hydrogencarbonate solution (160 mL) were added thereto, and the internal temperature was brought to approximately 40° C. with stirring.

After separation into an organic layer and an aqueous layer, a 20% aqueous sodium chloride solution (40 mL) was added to the organic layer, and the mixture was stirred for approximately 15 minutes. After separation into an organic layer and an aqueous layer, the organic layer was concentrated under reduced pressure until the amount of the solution became approximately 160 mL. The concentrate was cooled to an internal temperature of approximately 25° C. To the concentrate, acetone (280 mL) was then added, and subsequently, water (200 mL) was added dropwise over approximately 2 hours. The internal temperature was lowered to approximately 0° C. Then, the mixture was stirred for approximately 1.5 hours, and precipitates were collected by filtration, washed with aqueous acetone, and then dried to obtain 5-chloro-N-(2,4-dimethoxybenzyl)-2,4-difluoro-N-(pyrimidin-4-yl)benzenesulfonamide (58.5 g, yield: 89.7%).

1-3) 5-Chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide A mixture of (1S,2R)-2-(1-methyl-1H-pyrazol-5-yl)cyclohexanol (WO2013/118854; 12.00 g, 0.067 mol), 5-chloro-N-(2,4-dimethoxybenzyl)-2,4-difluoro-N-(pyrimidin-4-yl)benzenesulfonamide (31.87 g, 0.070 mol), and N,N-dimethylacetamide (300 mL) was cooled to an internal temperature of approximately −20° C. A suspension of potassium t-butoxide (8.22 g, 0.073 mol) in THF (66 mL) was added dropwise thereto at an internal temperature in the range of −20° C. to −10° C. over approximately 0.5 hours. After the completion of dropwise addition, the mixture was stirred for approximately 45 minutes. Subsequently, toluene (300 mL) and water (300 mL) were added thereto, and the mixture was stirred for approximately 0.5 hours. After separation into an organic layer and an aqueous layer, a 1% aqueous sodium hydroxide solution (300 mL) was added to the organic layer, and the organic layer was washed. This operation was repeated twice. The organic layer was further washed with water (300 mL), and the combined organic layer was then concentrated under reduced pressure until the amount of the solution became approximately 80 mL, to obtain a solution of the title compound in toluene.

1-4) 5-Chloro-2-fluoro-4-{[(1S,2R)-2-(1-methyl-1H-pyrazol-5-yl)cyclohexyl]oxy}-N-(pyrimidin-4-yl)benzenesulfonamide (Step of Removing 2,4-dimethoxybenzyl Group)

To a mixture of the solution of 5-chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide in toluene obtained in Example 1-3), acetonitrile (360 mL), and triphenylphosphine (17.46 g, 0.067 mol), 35% hydrochloric acid (34.68 g) was added dropwise at an internal temperature in the range of 20° C. to 30° C. over approximately 5 minutes. After the completion of dropwise addition, the mixture was stirred at an internal temperature of approximately 40° C. for approximately 3 hours. The reaction solution was cooled to approximately 25° C. Water (120 mL) and toluene (300 mL) were added thereto, and the mixture was stirred for approximately 10 minutes. After separation into an organic layer and an aqueous layer, acetonitrile (240 mL) and toluene (240 mL) were added to the aqueous layer, and the aqueous layer was washed. This operation was repeated twice. To the aqueous layer thus washed, activated carbon (1.8 g) was added, and the mixture was stirred for approximately 30 minutes. Then, activated carbon was filtered off and washed. The aqueous layer thus treated with activated carbon was concentrated under reduced pressure until the amount of the solution became approximately 240 mL.

The concentrate was cooled to an internal temperature of approximately 25° C. Then, ethanol (240 mL) was added thereto, and the pH was adjusted to approximately 1.3 with a 2 N aqueous sodium hydroxide solution. Then, the internal temperature was elevated to approximately 40° C. Seed crystals of 5-chloro-2-fluoro-4-{[(1S,2R)-2-(1-methyl-1H-pyrazol-5-yl)cyclohexyl]oxy}-N-(pyrimidin-4-yl)benzenesulfonamide (12 mg) were added thereto, and the mixture was stirred for approximately 2 hours. The internal temperature was lowered to approximately 25° C. Then, the pH was adjusted to approximately 4.0 with a 2 N aqueous sodium hydroxide solution. After stirring overnight, crystals were collected by filtration, washed, and then dried to obtain crystals of 5-chloro-2-fluoro-4-{[(1S,2R)-2-(1-methyl-1H-pyrazol-5-yl)cyclohexyl]oxy}-N-(pyrimidin-4-yl)benzenesulfonamide (25.32 g, yield: 81.6%).

The spectral data of the product was consistent with that described in WO2013/118854.

Example 2 5-Chloro-2-fluoro-4-{[(1S,2R)-2-(1-methyl-1H-pyrazol-5-yl)cyclohexyl]oxy}-N-(pyrimidin-4-yl)benzenesulfonamide To a solution of a powder of 5-chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide (5.0 g, 8.11 mmol), acetonitrile (60 mL), and triphenylphosphine (2.13 g, 8.12 mmol), 35% hydrochloric acid (3.3 mL, 76.7 mmol) was added, and the mixture was warmed to an internal temperature of approximately 40° C. and then stirred for approximately 3 hours with this temperature kept. The reaction solution was cooled to approximately 25° C. Water (20 mL) and toluene (60 mL) were added thereto, and the mixture was stirred for approximately 10 minutes. After separation into an organic layer and an aqueous layer, acetonitrile (37.5 mL) and toluene (37.5 mL) were added to the aqueous layer, and the aqueous layer was washed. This operation was repetitively performed three times. To the aqueous layer thus washed, activated carbon (0.29 g) was added, and the mixture was stirred for approximately 30 minutes. Then, activated carbon was filtered off and washed. The aqueous layer thus treated with activated carbon was further concentrated under reduced pressure until the amount of the solution became approximately 25 mL. The concentrate was cooled to an internal temperature of approximately 25° C. Then, ethanol (37.5 mL) was added thereto, and the pH was adjusted to approximately 1.3 with 2 N aqueous sodium hydroxide solution. Then, the internal temperature was elevated to approximately 40° C. Seed crystals of 5-chloro-2-fluoro-4-{[(1S,2R)-2-(1-methyl-1H-pyrazol-5-yl)cyclohexyl]oxy}-N-(pyrimidin-4-yl)benzenesulfonamide (12 mg) were added thereto, and the mixture was stirred for approximately 2 hours. The internal temperature was lowered to approximately 25° C. Then, the pH was adjusted to approximately 4.0 with a 2 N aqueous sodium hydroxide solution, and the mixture was stirred for approximately 3.5 hours. Then, crystals were collected by filtration, washed, and dried to obtain crystals of 5-chloro-2-fluoro-4-{[(1S,2R)-2-(1-methyl-1H-pyrazol-5-yl)cyclohexyl]oxy}-N-(pyrimidin-4-yl)benzenesulfonamide (2.72 g, yield: 71.9%).

Example 3

Removal of 2,4-dimethoxybenzyl group from N-(2,4-dimethoxybenzyl)-4-methyl-N-(pyrimidin-4-yl)benzenesulfonamide (compound A)

[Formula 29]

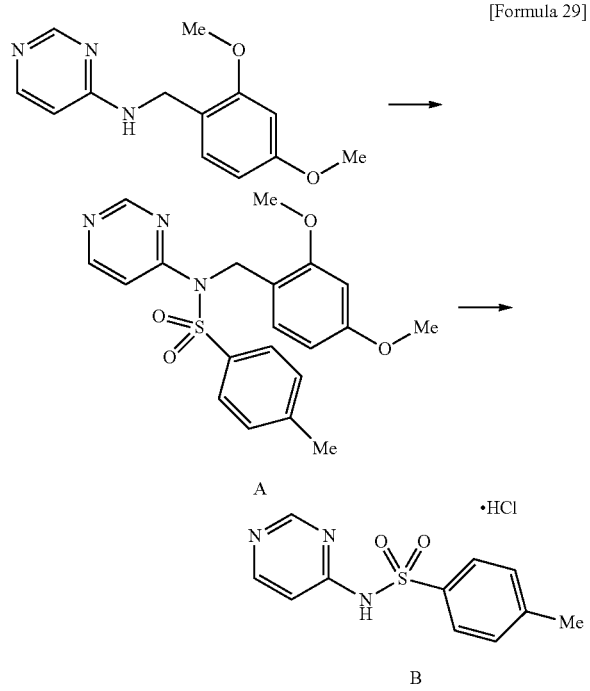

3-1) N-(2,4-Dimethoxybenzyl)-4-methyl-N-(pyrimidin-4-yl)benzenesulfonamide (Compound A)

To a solution of p-toluenesulfonyl chloride (4.04 g, 21.1 mmol) in ethyl acetate (20 ml), a solution of N-(2,4-dimethoxybenzyl)pyrimidin-4-amine (4.0 g, 16.31 mmol) produced in Example 1-1) and 1,4-diazabicyclo[2.2.2]octane (3.11 g, 27.7 mmol) in ethyl acetate (20 ml) was added dropwise, and the mixture was stirred at room temperature for 1 hour. To the reaction solution, a 5% aqueous sodium bicarbonate solution (16 mL) and ethyl acetate (12 ml) were added, followed by extraction. Then, the organic layer was washed with 20% saline (12 ml). After concentration under reduced pressure, the residue was purified by silica gel column chromatography (hexane/ethyl acetate: 1/2) to obtain the title compound (compound A; 6.35 g, 98%) as a white solid.

$^1$H-NMR (500 MHz, CDCl$_3$) δ ppm: 2.41 (3H, s), 3.76 (3H, s), 3.77 (3H, s), 5.23 (2H, s), 6.38-6.42 (2H, m), 7.15 (1H, d, J=8.5), 7.27 (2H, d, J=7.5 Hz), 7.35 (1H, dd, J=1.5, 6.0 Hz), 7.73 (2H, d, J=8 Hz), 8.45 (1H, d, J=6.0 Hz), 8.80 (1H, s).
MS(ESI) m/z: 400.1308[M+H]+.

3-2) 4-Methyl-N-(pyrimidin-4-yl)benzenesulfonamide (Compound B; Removal of 2,4-dimethoxybenzyl Group in Presence of triphenylphosphine)

To a solution of compound A (1.0 g, 2.50 mmol) synthesized in Example 3-1) and triphenylphosphine (656 mg, 2.50 mmol) in acetonitrile (15 ml), 35% hydrochloric acid (1.10 mL, 12.50 mmol) was added, and the mixture was stirred at approximately 40° C. for 6 hours. The reaction solution was cooled to room temperature, and precipitates were then collected by filtration and dried under reduced pressure to obtain compound B (650 mg, 91%) as a white solid.

$^1$H-NMR (500 MHz, DMSO-d$_6$) δ ppm: 2.37 (3H, s), 7.14 (1H, d, J=6.5 Hz), 7.41 (2H, d, J=8.5 Hz), 7.85 (2H, d, J=8 Hz), 8.46 (1H, d, J=6.5 Hz), 8.79 (1H, s).
MS(ESI) m/z: 248.0511[M−H]−.

3-3) N-(Pyrimidin-4-yl)-4-methylbenzenesulfonamide (Compound B; Removal of 2,4-dimethoxybenzyl Group in Absence of triphenylphosphine)

To a solution of compound A (1.5 g, 3.76 mmol) synthesized in Example 3-1) in acetonitrile (23 mL), 35% hydrochloric acid (1.66 mL, 18.80 mmol) was added, and the mixture was stirred at approximately 40° C. for 3 hours. The reaction solution was cooled to room temperature, and precipitates were then collected by filtration and then dried under reduced pressure to obtain compound B (1.45 g, 135%) as a white solid.

Quality Comparison
Compound B [Product of Example 3-2)]
A sample (10.92 mg) was collected into a volumetric flask. Aqueous acetonitrile (25 ml) was added thereto, and the mixture was ultrasonicated for approximately 2 minutes to obtain a test solution, which was then analyzed by HPLC.
Compound B [Product of Example 3-3)]
A sample (5.12 mg) was collected into a volumetric flask. Aqueous acetonitrile (25 ml) was added thereto, and the mixture was ultrasonicated for approximately 2 minutes. Then, insoluble matter was filtered off through a filter to obtain a test solution, which was then analyzed by HPLC.
HPLC (wavelength: 210 nm) analysis results
1) Area ratio
Product of Example 3-2): 100.0%
Product of Example 3-3): 96.1%
2) Relative purity comparison (area value/weighing value)

(Area value of the product of Example 3-3)/Weighing value of the product of Example 3-3))/(Area value of the product of Example 3-2)/Weighing value of the product of Example 3-2))×100=69 (%)

As is also evident from the need of the operation of filtering off insoluble matter during the preparation of the analysis sample, the product of Example 3-3) contained poorly soluble contaminants in the reaction product and exhibited approximately 30% reduction in purity as compared with the product of Example 3-2). By contrast, the product of Example 3-2) was free from the contamination of the reaction product by poorly soluble contaminants, demonstrating that the product was obtained with excellent purity by the reaction in the presence of triphenylphosphine.

Example 4 Removal of 2,4-dimethoxybenzyl Group from N-(2,4-dimethoxybenzyl)-4-methyl-N-(pyrimidin-2-yl)benzenesulfonamide (Compound D)

[Formula 30]

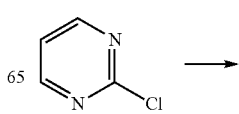

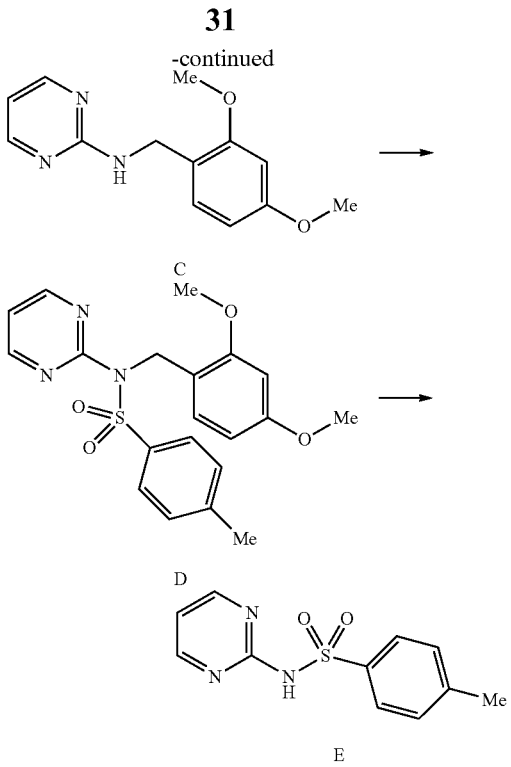

4-1) N-(2,4-Dimethoxybenzyl)pyrimidin-2-amine (Compound C)

To a solution of 2-chloropyrimidine (7.50 g, 65.5 mmol) and 2,4-dimethoxybenzylamine (10.95 g, 65.5 mmol) in 2-propanol (75 mL), triethylamine (13.7 mL, 98.3 mmol) was added, and the mixture was stirred at approximately 75° C. for 9 hours. The reaction solution was cooled to approximately 40° C. Then, water (75 mL) was slowly added thereto, and the mixture was cooled to room temperature. Water (37.5 mL) was further added thereto. Then, the mixture was cooled to approximately 5° C., and precipitates were collected by filtration and dried under reduced pressure to obtain compound C (12.20 g, yield: 76%) as a white solid.

$^1$H-NMR (500 MHz, CDCl$_3$) δ ppm: 3.79 (3H, s), 3.83 (3H, s), 4.55 (2H, d, J=6.0 Hz), 5.56 (1H, br s), 6.42 (1H, dd, J=2.5, 8.5 Hz), 6.46 (1H, d, J=2 Hz), 6.49 (1H, t, J=5 Hz), 7.23 (1H, d, J=8 Hz), 8.26 (2H, d, J=4.5 Hz).

4-2) N-(2,4-Dimethoxybenzyl)-4-methyl-N-(pyrimidin-2-yl)benzenesulfonamide (compound D)

A solution of compound C (4.0 g, 16.31 mmol) produced in Example 4-1) in THF (20 mL) was cooled to approximately −15° C. Then, a 1.0 M solution of lithium hexamethyldisilazide in THF (19.6 mL, 19.6 mmol) was added thereto, and the mixture was stirred at approximately −15° C. for 30 minutes, then stirred at approximately 0° C. for 10 minutes, and cooled again to approximately −10° C. Then, a solution of p-toluenesulfonyl chloride (4.0 g, 21.2 mmol) in THF (12 mL) was added dropwise thereto. The reaction solution was stirred at approximately 5° C. for 1 hour, and a 10% aqueous ammonium chloride solution (20 mL) and ethyl acetate (32 mL) were then added thereto, followed by extraction. The organic layer was washed with 20% saline (12 mL). After concentration under reduced pressure, the residue was purified by silica gel column chromatography (hexane/ethyl acetate: 1/1). The obtained solid was stirred in 2-propanol (16 mL) at approximately 45° C. for 30 minutes and then cooled to room temperature. Water (16 mL) was added thereto, and precipitates were then collected by filtration and dried under reduced pressure to obtain the title compound D (3.15 g, 48%) as a white solid.

$^1$H-NMR (500 MHz, CDCl$_3$) δ ppm: 2.38 (3H, s), 3.66 (3H, s), 3.78 (3H, s), 5.44 (2H, s), 6.37-6.39 (2H, m), 6.85 (1H, t, J=5.0 Hz), 7.11 (1H, d, J=8.5 Hz), 7.20 (2H, d, J=8.0 Hz), 7.85 (2H, J=8.5 Hz), 8.44 (2H, d, J=5.0).

MS(ESI) m/z: 400.1338[M+H]+.

4-3) 4-Methyl-N-(pyrimidin-2-yl)benzenesulfonamide (Compound E; Removal of 2,4-dimethoxybenzyl Group in Presence of triphenylphosphine)

To a solution of compound D (0.8 g, 2.0 mmol) produced in Example 4-2) and triphenylphosphine (525 mg, 2.0 mmol) in acetonitrile (16 mL), 35% hydrochloric acid (0.88 mL, 10.0 mmol) was added, and the mixture was stirred at approximately 40° C. for 3 hours. The reaction solution was cooled to room temperature and then concentrated under reduced pressure until the amount of the reaction solution became approximately 10 mL. Water (0.8 mL) was added to the concentrate, and the pH was then adjusted to 3.9 by the addition of an appropriate amount of a 2 N aqueous sodium hydroxide solution. Then, water (2.4 mL) was added thereto, and the mixture was stirred for 30 minutes. Precipitates were collected by filtration and dried under reduced pressure to obtain the title compound (301 mg, 60%) as a white solid.

$^1$H-NMR (500 MHz, CDCl$_3$) δ ppm: 2.41 (3H, s), 6.97 (1H, t, J=5.0 Hz), 7.28 (2H, t, J=8.5 Hz), 8.00 (2H, d, J=8.5 Hz), 8.65 (2H, d, J=5.0), 11.60 (1H, br s).

MS(ESI) m/z: 250.0662[M+H]+.

Example 5 Removal of 2,4-dimethoxybenzyl Group from 5-chloro-N-(2,4-dimethoxybenzyl)-2,4-difluoro-N-(pyrimidin-4-yl)benzenesulfonamide

[Formula 31]

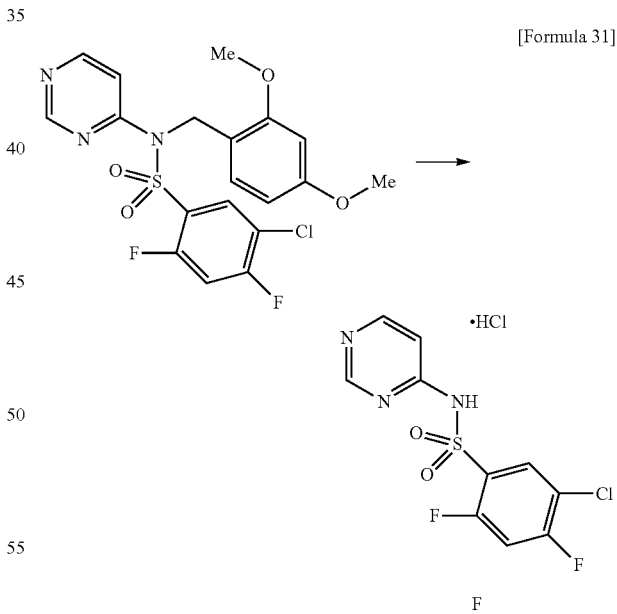

5-1) 5-Chloro-2,4-difluoro-N-(pyrimidin-4-yl)benzenesulfonamide hydrochloride (compound F; removal of 2,4-dimethoxybenzyl Group in Presence of triphenylphosphine)

To 5-chloro-N-(2,4-dimethoxybenzyl)-2,4-difluoro-N-(pyrimidin-4-yl)benzenesulfonamide (1.0 g, 2.19 mmol) produced in Example 1-2) and triphenylphosphine (574 mg, 2.19 mmol), acetonitrile (20 mL) was added, and the mixture was warmed to approximately 40° C. Then, 35% hydrochloric acid (0.97 mL, 10.95 mmol) was added thereto, and the mixture was stirred for 90 minutes. The reaction solution was cooled to room temperature, and precipitates were then collected by filtration and dried under reduced pressure to obtain the title compound (676 mg, 90%) as a slightly pink solid.

$^1$H-NMR (500 MHz, DMSO-$d_6$) δ ppm: 6.95 (1H, d, J=6.5 Hz), 7.72 (1H, t, J=9.5 Hz), 8.05 (1H, t, J=8.5), 8.22-8.23 (1H, m), 8.60 (1H, m), 13.01 (1H, br s).

MS(ESI) m/z: 305.9922[M+H]+.

5-2) 5-Chloro-2,4-difluoro-N-(pyrimidin-4-yl)benzenesulfonamide (Compound F; Removal of 2,4-dimethoxybenzyl Group in Presence of 1,3-diethyl-2-thiourea)

To a solution of 5-chloro-N-(2,4-dimethoxybenzyl)-2-fluoro-N-(pyrimidin-4-yl)benzenesulfonamide (1.0 g, 2.19 mmol) produced in Example 1-2) in acetonitrile (18 ml), 1,3-diethyl-2-thiourea (289 mg, 2.19 mmol) was added, and the mixture was warmed to approximately 40° C. Then, 35% hydrochloric acid (0.97 mL, 10.95 mmol) was added thereto, and the mixture was stirred for 1 hour. The reaction solution was cooled to room temperature, and precipitates were then collected by filtration and dried under reduced pressure to obtain the title compound (710 mg, 95%) as a slightly pink solid.

$^1$H-NMR (500 MHz, DMSO-$d_6$) δ ppm: 6.94 (1H, d, J=6.5 Hz), 7.72 (1H, t, J=10.0 Hz), 8.05 (1H, t, J=8.0), 8.20-8.21 (1H, m), 8.58 (1H, m), 12.20 (1H, br s).

MS(ESI) m/z: 305.9920[M+H]+.

Quality Comparison

Compound F [Product of Example 5-1)]

A sample (9.10 mg) was collected into a volumetric flask. Aqueous acetonitrile (25 ml) was added thereto, and the mixture was ultrasonicated for approximately 2 minutes to obtain a test solution, which was then analyzed by HPLC.

Compound F [Product of Example 5-2)]

A sample (9.21 mg) was collected into a volumetric flask. Aqueous acetonitrile (25 ml) was added thereto, and the mixture was ultrasonicated for approximately 2 minutes to obtain a test solution, which was then analyzed by HPLC.

HPLC (wavelength: 210 nm) analysis results

1) Area ratio

Product of Example 5-1): 97.8%

Product of Example 5-2): 97.9%

2) Relative purity comparison (area value/weighing value)

(Area value of the product of Example 5-2)/Weighing value of the product of Example 5-2))/(Area value of the product of Example 5-1)/Weighing value of the product of Example 5-1))×100=98 (%)

The product of Example 5-1) and the product of Example 5-2) were shown to have the same level of purity. This demonstrated that thiourea also has the effect of suppressing the formation of poorly soluble contaminants, as with triphenylphosphine.

Example 6 Removal of 2,4-dimethoxybenzyl Group from N-(2,4-dimethoxybenzyl)-2,4,5-trifluoro-N-(5-fluoropyrimidin-2-yl)benzenesulfonamide (Compound G)

[Formula 32]

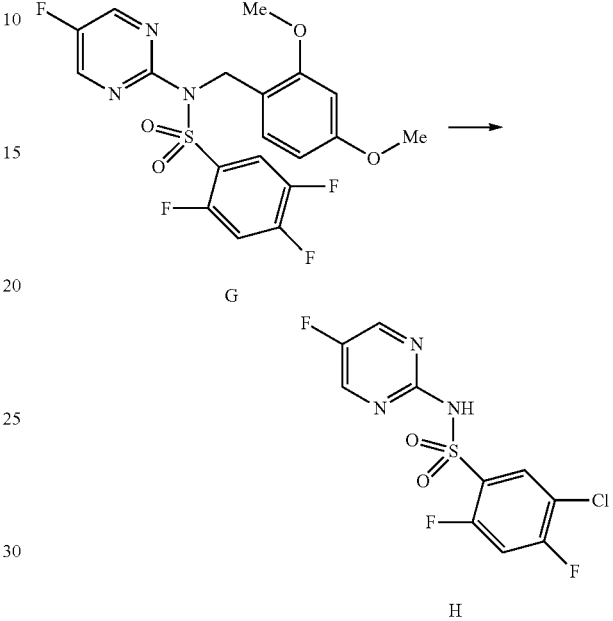

To a solution of compound G (0.30 g, 0.656 mmol) produced by a known method and triphenylphosphine (172 mg, 0.656 mmol) in acetonitrile (4.5 mL), 35% hydrochloric acid (0.29 mL, 3.28 mmol) was added, and the mixture was warmed to approximately 40° C. and then stirred for 3 hours. 35% hydrochloric acid (0.06 mL, 0.656 mmol) was further added thereto, and the mixture was stirred for 1 hour. Then, 35% hydrochloric acid (0.06 mL, 0.656 mmol) was further added thereto, and the mixture was stirred for 1 hour. The reaction solution was cooled to approximately 10° C., and precipitates were then collected by filtration and dried under reduced pressure to obtain 2,4,5-trifluoro-N-(5-fluoropyrimidin-2-yl)benzenesulfonamide (compound H; 121 mg, 60%) as a white solid.

$^1$H-NMR (500 MHz, DMSO-$d_6$) δ ppm: 7.81-7.86 (1H, m), 8.02-8.07 (1H, m), 8.64 (2H, d, J=1 Hz), 12.54 (1H, br s).

MS(ESI) m/z: 305.9960[M−H]−.

Example 7 Removal of 2,4-dimethoxybenzyl Group from N-(2,4-dimethoxybenzyl)-4-methyl-N-(pyridin-2-yl)benzenesulfonamide (Compound J)

[Formula 33]

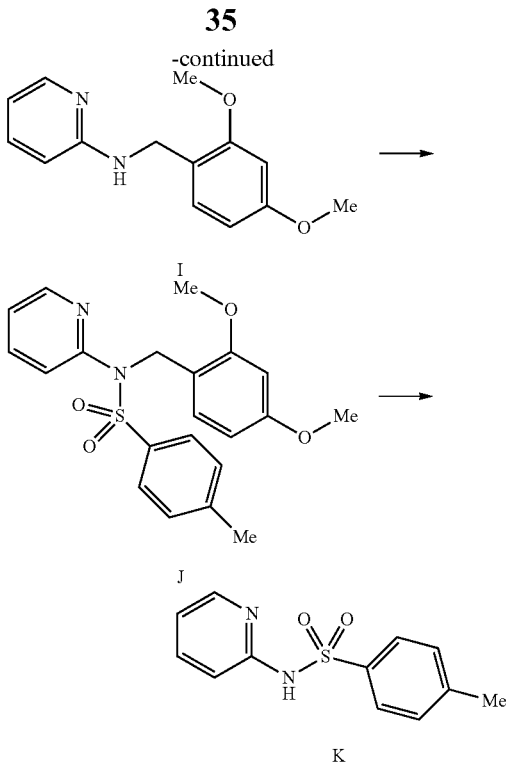

7-1) N-(2,4-Dimethoxybenzyl)pyridin-2-amine (Compound I)

To a solution of 2-aminopyridine (5.0 g, 53.1 mmol) and 2,4-dimethoxybenzaldehyde (10.59 g, 63.73 mmol) in toluene (50 mL), acetic acid (6.1 mL, 106.2 mmol) was added, and the mixture was stirred at approximately 105° C. for 1.5 hours. The reaction solution was cooled to approximately 35° C. Then, sodium triacetoxyborohydride (15.8 g, 74.4 mmol) was added thereto, and the mixture was stirred at approximately 30° C. for 30 minutes. To the reaction solution, ethyl acetate (100 mL), a 25% aqueous sodium hydroxide solution (35 mL) and water (25 mL) were added, followed by extraction. Then, the organic layer was washed with 20% saline (15 mL). After concentration under reduced pressure, the residue was purified by silica gel column chromatography (hexane/ethyl acetate: 2/3) to obtain the title compound (10.61 g, 82%) as a white solid.

$^1$H-NMR (500 MHz, CDCl$_3$) δ ppm: 3.79 (3H, s), 3.83 (3H, s), 4.41 (2H, d, J=6 Hz), 4.90 (1H, br s), 6.39 (1H, d, J=8.5 Hz), 6.42 (1H, dd, J=2.5, 8.0), 6.47 (1H, d, J=3.0 Hz), 6.53-6.55 (1H, m), 7.21 (1H, d, J=8.0 Hz), 7.36-7.40 (1H, m), 8.08-8.09 (1H, m).

7-2) N-(2,4-Dimethoxybenzyl)-4-methyl-N-(pyridin-2-yl)benzenesulfonamide (Compound J)

A solution of compound I (4.0 g, 16.4 mmol) produced in Example 7-1) in THF (20 mL) was cooled to approximately −15° C. Then, a 1.0 M solution of lithium hexamethyldisilazide in THF (19.6 mL) was added thereto, and the mixture was stirred for 30 minutes and then stirred at approximately 0° C. for 10 minutes. A solution of p-toluenesulfonyl chloride (4.06 g, 21.3 mmol) in THF (12 mL) was added dropwise thereto. The reaction solution was stirred at approximately 5° C. for 1 hour, and a 10% aqueous ammonium chloride solution (16 mL) and ethyl acetate (32 mL) were added thereto, followed by extraction. The organic layer was washed with 20% saline (12 mL). After concentration under reduced pressure, the residue was purified by silica gel column chromatography (hexane/ethyl acetate: 1/1). The obtained solid was stirred in 2-propanol (16 mL) at room temperature. Then, water (16 mL) was added thereto, and the resulting solid was collected by filtration and dried under reduced pressure to obtain the title compound (4.92 g, 75%) as a white solid.

$^1$H-NMR (500 MHz, CDCl$_3$) δ ppm: 2.40 (3H, s), 3.67 (3H, s), 3.74 (3H, s), 4.95 (2H, S), 6.34-6.36 (2H, m), 7.05-7.08 (1H, m), 7.22-7.25 (3H, m), 7.46 (1H, d, J=8.0 Hz), 7.57 (2H, d, J=8.5), 7.61-7.64 (1H, m), 8.28-8.30 (1H, m).

MS(ESI) m/z: 399.1393[M+H]+.

7-3) 4-Methyl-N-(pyridin-2-yl)benzenesulfonamide (Compound K)

To a solution of compound J (0.7 g, 1.76 mmol) produced in Example 7-2) and triphenylphosphine (462 mg, 1.76 mmol) in acetonitrile (10.5 ml), 35% hydrochloric acid (0.78 mL, 8.80 mmol) was added, and the mixture was stirred at approximately 40° C. for 1 hour. The reaction solution was cooled to room temperature and then concentrated under reduced pressure until the amount of the reaction solution became approximately 6 mL. Water (1.4 mL) was added to the concentrate, and the pH was adjusted to 2.7 by the addition of an appropriate amount of a 2 N aqueous sodium hydroxide solution. Then, the mixture was stirred for 30 minutes. Precipitates were collected by filtration and dried under reduced pressure to obtain the title compound (367 mg, 84%) as a white solid.

$^1$H-NMR (500 MHz, DMSO-d$_6$) δ ppm: 2.34 (3H, s), 6.87 (1H, t, J=6.0 Hz), 7.14 (1H, d, J=8.5), 7.33 (2H, d, J=8.0 Hz), 7.68-7.72 (1H, m), 7.76 (2H, dd, J=2.0, 7.0 Hz), 8.01-8.02 (1H, m), 11.83 (1H, br s).

MS(ESI) m/z: 249.0705[M+H]+.

Example 8 Removal of 2,4-dimethoxybenzyl Group from N-(2,4-dimethoxybenzyl)-4-methyl-N-(1,3-thiazol-2-yl)benzenesulfonamide (Compound M)

[Formula 34]

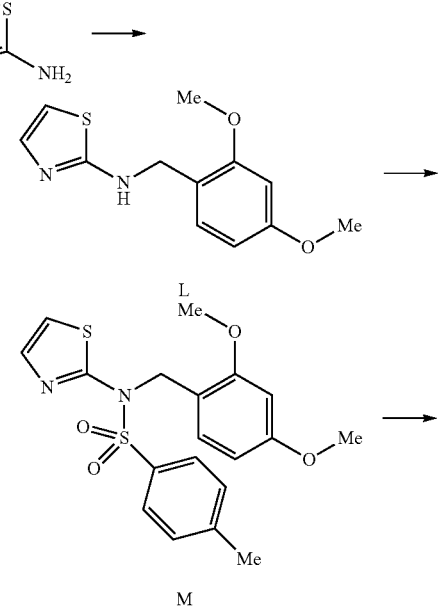

-continued

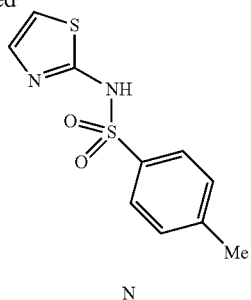

N 8-1) N-(2,4-Dimethoxybenzyl)-1,3-thiazol-2-amine (Compound L)

A solution of 2-aminothiazole (5.0 g, 49.9 mmol) and 2,4-dimethoxybenzaldehyde (9.96 g, 59.9 mmol) in toluene (60 mL) was stirred at approximately 105° C. for 30 minutes. The reaction solution was cooled to approximately 35° C. Then, sodium triacetoxyborohydride (14.8 g, 69.9 mmol) was added thereto, and the mixture was stirred at approximately 35° C. for 30 minutes. To the reaction solution, ethyl acetate (100 mL) and water (50 mL) were added, followed by extraction. Then, the organic layer was concentrated under reduced pressure, and the residue was purified by silica gel column chromatography (hexane/ethyl acetate: 1/1). 2-Propanol (20 mL) was added to the obtained solid, and the mixture was stirred at room temperature for 15 minutes. Water (50 mL) was added thereto, and the mixture was stirred for 30 minutes. Then, the resulting solid was collected by filtration and dried under reduced pressure to obtain the title compound (8.13 g, 65%) as a white solid.

$^1$H-NMR (500 MHz, CDCl$_3$) δ ppm: 3.79 (3H, s), 3.82 (3H, s), 4.38 (2H, s), 5.69 (1H, br s), 6.43 (1H, dd, J=2.0, 8.0 Hz), 6.46-6.47 (2H, m), 7.09 (1H, d, J=3.5 Hz), 7.22 (1H, d, J=8.0 Hz).

8-2) N-(2,4-Dimethoxybenzyl)-4-methyl-N-(1,3-thiazol-2-yl)benzenesulfonamide (Compound M)

A solution of compound L (4.0 g, 16.0 mmol) produced in Example 8-1) in THF (20 mL) was cooled to approximately −15° C. A 1.0 M solution of lithium hexamethyldisilazide in THF (19.2 mL, 19.2 mmol) was added thereto, and the mixture was stirred for 20 minutes and then stirred at approximately 0° C. for 10 minutes. Subsequently, a solution of p-toluenesulfonyl chloride (4.0 g, 20.8 mmol) in THF (12 mL) was added dropwise thereto. The reaction solution was stirred at approximately 5° C. for 30 minutes, and a 10% aqueous ammonium chloride solution (16 mL) and ethyl acetate (32 mL) were then added thereto, followed by extraction. The organic layer was washed with 20% saline (12 mL). After concentration under reduced pressure, the residue was purified twice by silica gel column chromatography (hexane/ethyl acetate: 1/1) to obtain the title compound (3.08 g, 48%) as a white solid.

$^1$H-NMR (500 MHz, CDCl$_3$) δ ppm: 2.41 (3H, s), 3.73 (3H, s), 3.76 (3H, s), 5.05 (2H, s), 6.35-6.37 (2H, m), 6.98 (1H, d, J=3.5 Hz), 7.17 (1H, d, J=8.0 Hz), 7.26 (2H, d, J=8.5 Hz), 7.38 (1H, d, J=3.5 Hz), 7.70 (2H, d, J=8.0 Hz)

MS(ESI) m/z: 405.0941[M+H]+.

8-3) 4-Methyl-N-(1,3-thiazol-2-yl)benzenesulfonamide (Compound N)

To a solution of compound M (0.7 g, 1.73 mmol) produced in Example 8-2) and triphenylphosphine (454 mg, 1.73 mmol) in acetonitrile (10.5 ml), 35% hydrochloric acid (0.76 mL, 8.65 mmol) was added, and the mixture was stirred at room temperature for 1 hour. Precipitates were collected by filtration and dried under reduced pressure to obtain the title compound (145 mg, 33%) as a white solid.

$^1$H-NMR (500 MHz, DMSO-d$_6$) δ ppm: 2.35 (3H, s), 6.81 (1H, d, J=4.5 Hz), 7.24 (1H, d, J=4.5), 7.33 (2H, dJ=8.0 Hz), 7.68 (2H, d, J=8.0 Hz), 12.68 (1H, br s).

MS(ESI) m/z: 255.0273[M+H]+.

Example 9 5-Chloro-2-fluoro-4-{[(1S,2R,5S)-5-hydroxy-2-(1-methyl-1H-pyrazol-5-yl)cyclohexyl]oxy}-N-(pyrimidin-4-yl)benzenesulfonamide

[Formula 35]

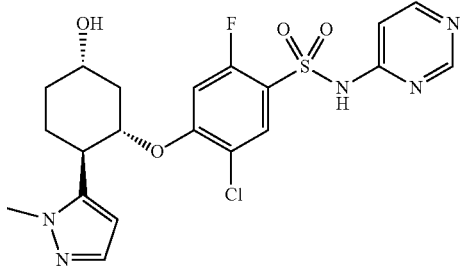

9-1) 5-Chloro-N-(2,4-dimethoxybenzyl)-2-fluoro-4-{[(1S,2R,5S)-5-hydroxy-2-(1-methyl-1H-pyrazol-5-yl)cyclohexyl]oxy}-N-(pyrimidin-4-yl)benzenesulfonamide Known 5-chloro-N-(2,4-dimethoxybenzyl)-2-fluoro-4-{[(1S*,2R*,5S*)-5-hydroxy-2-(1-methyl-1H-pyrazol-5-yl)cyclohexyl]oxy}-N-(pyrimidin-4-yl)benzenesulfonamide (415 mg, 0.657 mmol) was optically resolved with CHIRALFLASH IA (CPI Company/Daicel Corp.; hexane/isopropanol=4:6) to obtain a highly polar compound (136 mg) and a low polar compound (129 mg).

9-2) 5-Chloro-2-fluoro-4-{[(1S,2R,5S)-5-hydroxy-2-(1-methyl-1H-pyrazol-5-yl)cyclohexyl]oxy}-N-(pyrimidin-4-yl)benzenesulfonamide To a solution of 5-chloro-N-(2,4-dimethoxybenzyl)-2-fluoro-4-{[(1S,2R,5S)-5-hydroxy-2-(1-methyl-1H-pyrazol-5-yl)cyclohexyl]oxy}-N-(pyrimidin-4-yl)benzenesulfonamide (low polar compound; 1.00 g, 1.58 mmol) produced in Example 9-1) in toluene (6.5 mL) and acetonitrile (30 mL), triphenylphosphine (415 mg, 1.58 mL) and concentrated hydrochloric acid (35%, 240 µL, 7.91 mmol) were added at room temperature, and the reaction solution was stirred at 40° C. for 2 hours. The reaction solution was cooled to room temperature, and water (100 mL) was then added thereto. After separation, the aqueous layer was subjected to extraction with 1 M hydrochloric acid (100 mL). The aqueous layer was washed three times with a mixed solvent of toluene and acetonitrile (1:1), and a 1 M aqueous sodium hydroxide solution was then added thereto (pH=4). The aqueous layer was subjected to extraction with dichloromethane twice. The organic layer was dried over anhydrous sodium sulfate, then concentrated under reduced pressure, and crystallized with ethyl acetate to obtain the title compound (261 mg, 34%) as white crystals.

$^1$H-NMR (500 MHz, CD$_3$OD) δ ppm: 1.45-1.75 (3H, m), 1.97-2.08 (2H, m), 2.43-2.46 (1H, m), 3.10-3.15 (1H, m), 3.81-3.86 (1H, m), 3.88 (3H, s), 4.56 (1H, dt, J=3.9, 10.7 Hz), 6.13 (1H, s), 6.96-7.01 (2H, m), 7.25 (1H, s), 7.91 (1H, d, J=7.3 Hz), 8.25 (1H, d, J=6.4 Hz), 8.53 (1H, s);

MS(ESI) m/z: 482[M+H]+;

Anal. calcd for C$_{20}$H$_{21}$ClFN$_5$O$_4$S: C, 49.84; H, 4.39; N, 14.53. Found C, 49.74; H, 4.49; N, 14.36; [α]$_D^{20}$=28.75 (c 1.02, DMSO).

Example 10 5-Chloro-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide

[Formula 36]

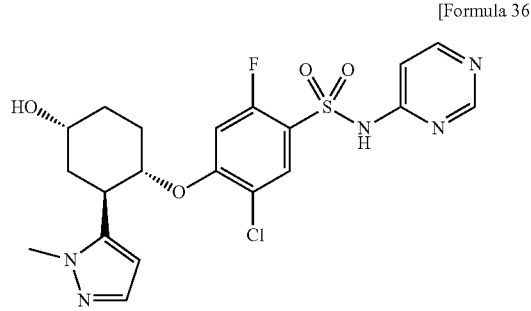 [SMILES: Cn1nccc1[C@H]1C[C@H](O)CC[C@@H]1Oc1cc(F)c(S(=O)(=O)Nc2ccncn2)cc1Cl]

To a solution of known 5-chloro-N-(2,4-dimethoxybenzyl)-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide (1.00 g, 1.58 mmol) in toluene (6.5 mL) and acetonitrile (30 mL), triphenylphosphine (415 mg, 1.58 mL) and concentrated hydrochloric acid (35%, 240 µL, 7.91 mmol) were added at room temperature, and the reaction solution was stirred at 40° C. for 2 hours. The reaction solution was cooled to room temperature, and water (100 mL) was then added thereto. After separation, the aqueous layer was subjected to extraction with 1 M hydrochloric acid (100 mL). The aqueous layer was washed three times with a mixed solvent of toluene and acetonitrile (1:1), and a 1 M aqueous sodium hydroxide solution was then added thereto (pH=4). The aqueous layer was subjected to extraction with dichloromethane twice. The organic layer was dried over anhydrous sodium sulfate, then concentrated under reduced pressure, and crystallized with ethyl acetate and hexane to obtain the title compound (458 mg, 60%) as white crystals.

$^1$H-NMR (500 MHz, CD$_3$OD) δ ppm: 1.77-2.04 (6H, m), 3.56-3.61 (1H, m), 3.90 (3H, s), 4.10-4.13 (1H, m), 4.51-4.56 (1H, m), 6.15 (1H, d, J=2.0 Hz), 6.97 (1H, d, J=12.2 Hz), 7.00 (1H, d, J=6.4 Hz), 7.26 (1H, d, J=2.0 Hz), 7.90 (1H, d, J=7.3 Hz), 8.25 (1H, d, J=6.4 Hz), 8.53 (1H, s);

MS(ESI) m/z: 482[M+H]+;

Anal. calcd for C$_{20}$OH$_{21}$ClFN$_5$O$_4$S0.1H$_2$O: C, 49.66; H, 4.42; N, 14.48. Found C, 49.51; H, 4.48; N, 14.26; [α]$_D^{25}$=9.62 (c 0.915, DMSO).

Example 11 5-Chloro-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide

[Formula 37]

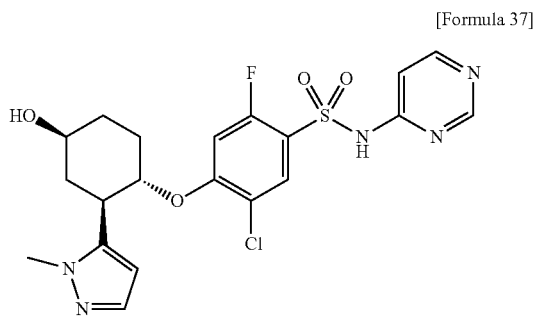 [SMILES: Cn1nccc1[C@H]1C[C@@H](O)CC[C@@H]1Oc1cc(F)c(S(=O)(=O)Nc2ccncn2)cc1Cl]

11-1) 5-Chloro-N-(2,4-dimethoxybenzyl)-2-fluoro-4-{[(1S,2R)-2-(1-methyl-1H-pyrazol-5-yl)-4-oxocyclohexyl]oxy}-N-(pyrimidin-4-yl)benzenesulfonamide To a solution of known 5-chloro-N-(2,4-dimethoxybenzyl)-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide (7.03 g, 11.1 mmol) in dichloromethane (300 mL), Dess-Martin periodinane (10.4 g, 24.5 mmol) was added at 0° C., and the reaction solution was stirred at room temperature for 2 hours. To the reaction solution, a saturated aqueous solution of sodium hydrogencarbonate and an aqueous sodium thiosulfate solution were added, followed by extraction with dichloromethane twice. The organic layer was dried over anhydrous sodium sulfate and concentrated under reduced pressure, and the residue was then purified by silica gel column chromatography (hexane/acetone: 50:50) to obtain the title compound (7.01 g, 99%) as a colorless amorphous solid.

$^1$H-NMR (400 MHz, CDCl$_3$) δ ppm: 2.09-2.17 (1H, m), 2.24-2.31 (1H, m), 2.47-2.54 (1H, m), 2.62-2.73 (2H, m), 2.97 (1H, ddd, J=1.6, 5.9, 15.7 Hz), 3.68-3.74 (1H, m), 3.77 (3H, s), 3.78 (3H, s), 3.91 (3H, s), 4.63 (1H, td, J=3.1, 7.0 Hz), 5.23 (2H, s), 6.10 (1H, d, J=2.0 Hz), 6.39-6.42 (2H, m), 6.60 (1H, d, J=11.0 Hz), 7.19-7.21 (2H, m), 7.41 (1H, d, J=2.0 Hz), 8.05 (1H, d, J=7.4 Hz), 8.48 (1H, d, J=5.9 Hz), 8.80 (1H, d, J=0.8 Hz).

11-2) 5-Chloro-N-(2,4-dimethoxybenzyl)-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide To a solution of 5-chloro-N-(2,4-dimethoxybenzyl)-2-fluoro-4-{[(1S,2R)-2-(1-methyl-1H-pyrazol-5-yl)-4-oxocyclohexyl]oxy}-N-(pyrimidin-4-yl)benzenesulfonamide (7.01 g, 11.1 mmol) produced in Example 11-1) in ethanol (200 mL), sodium borohydride (505 mg, 13.4 mmol) was added at 0° C., and the reaction solution was stirred at 0° C. for 30 minutes. To the reaction solution, water was added, and the mixture was concentrated under reduced pressure. Then, the residue was subjected to extraction with ethyl acetate twice. The organic layer was dried over anhydrous sodium sulfate and concentrated under reduced pressure, and the residue was then crystallized (hexane and ethyl acetate) to obtain the title compound (4.77 g, 68%) as white crystals.

$^1$H-NMR (500 MHz, CDCl$_3$) δ ppm: 1.49-1.79 (3H, m), 2.14-2.28 (3H, m), 3.16-3.21 (1H, m), 3.76 (6H, s), 3.86-3.92 (1H, m), 3.92 (3H, s), 4.11-4.18 (1H, m), 5.20 (2H, s), 6.07 (1H, d, J=2.0 Hz), 6.39-6.42 (3H, m), 7.17-7.21 (2H, m), 7.36 (1H, d, J=2.0 Hz), 7.94 (1H, d, J=7.3 Hz), 8.46 (1H, d, J=5.9 Hz), 8.79 (1H, d, J=1.0 Hz).

11-3) 5-Chloro-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide To a solution of 5-chloro-N-(2,4-dimethoxybenzyl)-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide (1.00 g, 1.58 mmol) produced in Example 11-2) in toluene (6.5 mL) and acetonitrile (30 mL), triphenylphosphine (415 mg, 1.58 mL) and concentrated hydrochloric acid (35%, 240 μL, 7.91 mmol) were added at room temperature, and the reaction solution was stirred at 40° C. for 2 hours. The reaction solution was cooled to room temperature, and water (100 mL) was then added thereto. After separation, the aqueous layer was subjected to extraction with 1 M hydrochloric acid (100 mL). The aqueous layer was washed three times with a mixed solvent of toluene and acetonitrile (1:1), and a 1 M aqueous sodium hydroxide solution was then added thereto (pH=4). The aqueous layer was subjected to extraction with dichloromethane twice. The organic layer was dried over anhydrous sodium sulfate, then concentrated under reduced pressure, and crystallized with ethyl acetate and hexane to obtain the title compound (391 mg, 51%) as white crystals.

$^1$H-NMR (500 MHz, CD$_3$OD) δ ppm: 1.56-1.77 (3H, m), 2.06-2.22 (3H, m), 3.79-3.85 (1H, m), 3.88 (3H, s), 4.50-4.55 (1H, m), 4.81-4.89 (1H, m), 6.18 (1H, d, J=2.0 Hz), 6.95-7.00 (2H, m), 7.26 (1H, d, J=2.0 Hz), 7.90 (1H, d, J=7.3 Hz), 8.25 (1H, d, J=5.9 Hz), 8.52 (1H, s);

MS(ESI/APCI) m/z: 482[M+H]+. [α]$_D^{20}$=−5.71 (c 1.004, MeOH).

INDUSTRIAL APPLICABILITY

In a method for producing a de-dimethoxybenzylated compound, comprising treating a compound containing a dimethoxybenzyl group bonded to a nitrogen atom with an acid to remove the dimethoxybenzyl group, the reaction can be carried out in the presence of triphenylphosphine or diethylthiourea to thereby suppress the production of a poorly soluble product considered to be formed from the removed dimethoxybenzyl group. Thus, the de-dimethoxybenzylated compound having excellent quality can be obtained without complex operation.

The invention claimed is:

1. A method for producing a de-dimethoxybenzylated compound, comprising treating a compound containing a dimethoxybenzyl group bonded to a nitrogen atom with an acid to remove the dimethoxybenzyl group, wherein the method is carried out in the presence of triphenylphosphine or diethylthiourea.

2. The method according to claim 1, wherein the removal of the dimethoxybenzyl group is carried out in the presence of triphenylphosphine.

3. The method according to claim 1, wherein the dimethoxybenzyl group is a 2,4-dimethoxybenzyl group.

4. The method according to claim 1, wherein the acid is a strong acid.

5. The method according to claim 1, wherein the acid is hydrochloric acid.

6. The method according to claim 1, wherein the nitrogen atom to which the dimethoxybenzyl group is bonded is a nitrogen atom constituting a sulfonamide group.

7. The method according to claim 6, wherein the sulfonamide group with the dimethoxybenzyl group bonded to the nitrogen atom is a sulfonamide group of a benzenesulfonamide compound.

8. The method according to claim 7, wherein the benzenesulfonamide compound having the sulfonamide group with the dimethoxybenzyl group bonded to the nitrogen atom is 5-chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide, 5-chloro-N-(2,4-dimethoxybenzyl)-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide, 5-chloro-N-(2,4-dimethoxybenzyl)-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide, or 5-chloro-N-(2,4-dimethoxybenzyl)-2-fluoro-4-{[(1S,2R,5S)-5-hydroxy-2-(1-methyl-1H-pyrazol-5-yl)cyclohexyl]oxy}-N-(pyrimidin-4-yl)benzenesulfonamide.

9. A method for producing a compound represented by Formula 2, comprising treating a compound represented by Formula 1 in which a nitrogen atom is substituted by a dimethoxybenzyl group:

[Formula 1]

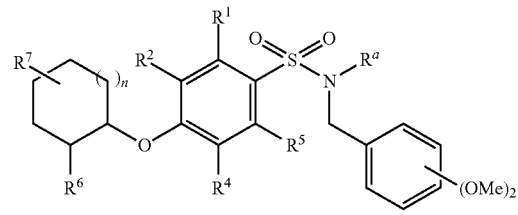

wherein R$^a$ represents an aromatic group optionally having a substituent(s), R$^1$, R$^2$, R$^4$ and R$^5$ each independently represent a hydrogen atom, a halogen atom, or an alkyl group having a carbon number of 1 to 6, R$^6$ represents an aromatic group optionally having a substituent(s), R$^7$ represents a hydrogen atom, a hydroxyl group, or one or two halogen atoms, and n represents an integer of 0, 1, or 2 in the presence of an acid and in the presence of triphenylphosphine or diethylthiourea to produce the compound represented by Formula 2:

[Formula 2]

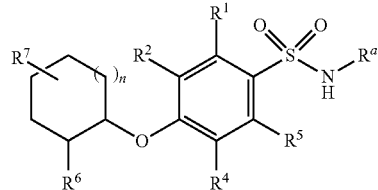

wherein R$^a$, R$^1$, R$^2$, R$^4$, R$^5$, R$^6$, R$^7$ and n are as defined above.

10. The method according to claim 9, wherein the compound represented by Formula 1:

[Formula 1]

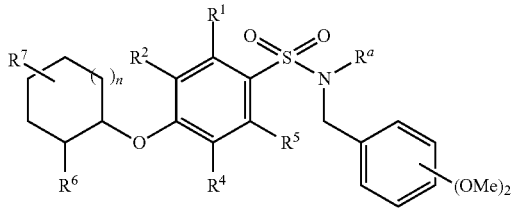

has a structure represented by Formula 4:

[Formula 4]

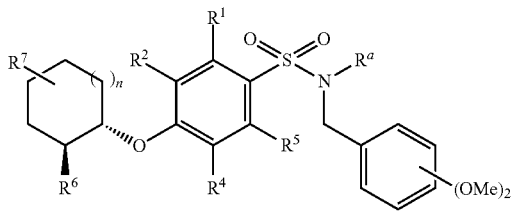

and the compound represented by Formula 2:

[Formula 2]

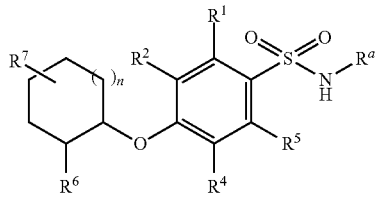

has a structure represented by Formula 6:

[Formula 6]

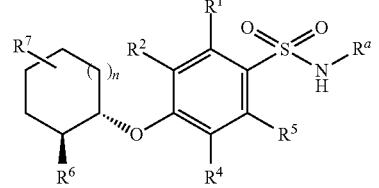

wherein $R^a$, $R^1$, $R^2$, $R^4$, $R^5$, $R^6$, $R^7$ and n are as defined above.

11. The method according to claim 9, wherein the treatment occurs in the presence of coexisting triphenylphosphine.

12. The method according to claim 9, wherein the dimethoxybenzyl group is a 2,3-dimethoxybenzyl group, a 2,4-dimethoxybenzyl group, a 2,5-dimethoxybenzyl group, a 2,6-dimethoxybenzyl group, a 3,4-dimethoxybenzyl group, or a 3,5-dimethoxybenzyl group.

13. The method according to claim 9, wherein the dimethoxybenzyl group is a 2,4-dimethoxybenzyl group.

14. The method according to claim 9, wherein the acid is a strong acid.

15. The method according to claim 9, wherein the acid is hydrochloric acid, methanesulfonic acid, trifluoromethanesulfonic acid, benzenesulfonic acid, toluenesulfonic acid, or trifluoroacetic acid.

16. The method according to claim 9, wherein the acid is hydrochloric acid.

17. The method according to claim 9, wherein $R^a$ is an aromatic heterocyclic group optionally having a substituent(s).

18. The method according to claim 17, wherein $R^a$ is a thiazolyl group, thiadiazolyl group, or pyrimidyl group optionally having a substituent(s).

19. The method according to claim 18, wherein $R^a$ is a 2-pyrimidyl group or 4-pyrimidyl group optionally having a substituent(s).

20. The method according to claim 18, wherein $R^a$ is a 4-pyrimidyl group optionally having a substituent(s).

21. The method according to claim 9, wherein n is 1.

22. The method according to claim 9, wherein $R^6$ is a phenyl group, pyrazolyl group, imidazolyl group, pyridyl group, or pyridazinyl group optionally having a substituent(s).

23. The method according to claim 9, wherein $R^6$ is a pyrazolyl group optionally having a substituent(s).

24. The method according to claim 9, wherein $R^6$ is a 1H-pyrazol-5-yl group optionally having a substituent(s).

25. The method according to claim 23, wherein the substituent(s) on the aromatic group optionally having a substituent(s), represented by $R^6$ is 1 to 3 groups selected from the group consisting of an amino group, a methyl group, an ethyl group, a fluorine atom and a chlorine atom.

26. The method according to claim 9, wherein $R^6$ is a 1-methyl-1H-pyrazol-5-yl group.

27. The method according to claim 9, wherein $R^7$ is a hydrogen atom.

28. The method according to claim 9, wherein $R^7$ is a hydroxyl group.

29. The method according to claim 9, wherein the compound represented by Formula 1:

[Formula 1]

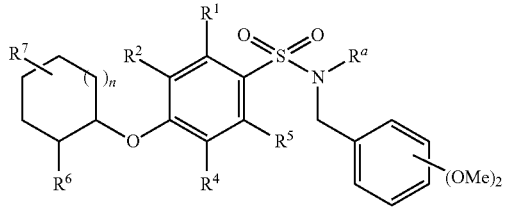

is 5-chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide, 5-chloro-N-(2,4-dimethoxybenzyl)-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide, 5-chloro-N-(2,4-dimethoxybenzyl)-2-fluoro-4-{[(1S,2R,4S)-4-hydroxy-2-(1-methyl-1H-pyrazol-5-yl)cyclohexyl]oxy}-N-(pyrimidin-4-yl)benzenesulfonamide, or 5-chloro-N-(2,4-dimethoxybenzyl)-2-fluoro-4-{[(1S,2R,5S)-5-hydroxy-2-(1-methyl-1H-pyrazol-5-yl)cyclohexyl]oxy}-N-(pyrimidin-4-yl)benzenesulfonamide.

* * * * *